US005683691A

United States Patent [19]

Peferoen et al.

[11] Patent Number: 5,683,691

[45] Date of Patent: Nov. 4, 1997

[54] *BACILLUS THURINGIENSIS* INSECTICIDAL TOXINS

[75] Inventors: Marnix Peferoen, Leuven; Bart Lambert, Beernem; Henk Joos, Aalter, all of Belgium

[73] Assignee: Plant Genetic Systems, N.V., Gent, Belgium

[21] Appl. No.: 462,319

[22] Filed: Jun. 5, 1995

Related U.S. Application Data

[63] Continuation of Ser. No. 247,459, May 23, 1994, abandoned, which is a continuation of Ser. No. 741,440, Aug. 6, 1991, abandoned.

[30] Foreign Application Priority Data

Feb. 15, 1989 [EP] European Pat. Off. .............. 89400428

[51] Int. Cl.$^6$ .................................................. C12N 1/20

[52] U.S. Cl. .............................. 424/93.461; 435/252.5; 435/832; 530/350; 530/825

[58] Field of Search .................... 424/93.461; 435/252.5, 435/832; 530/350, 825

[56] References Cited

U.S. PATENT DOCUMENTS

| | | | |
|---|---|---|---|
| 4,766,203 | 8/1988 | Kriej et al. | 424/93.461 |
| 4,771,131 | 9/1988 | Herrnstadt et al. | 536/23.71 |
| 4,797,276 | 1/1989 | Herrnstadt et al. | 424/84 |
| 4,902,507 | 2/1990 | Morris et al. | 424/93.461 |
| 4,966,765 | 10/1990 | Payne et al. | 424/93.461 |
| 4,996,155 | 2/1991 | Sick et al. | 424/93.2 |
| 4,999,192 | 3/1991 | Payne et al. | 424/93.461 |

FOREIGN PATENT DOCUMENTS

| | | |
|---|---|---|
| 0193 259 | 9/1986 | European Pat. Off. . |
| 0 213 818 | 3/1987 | European Pat. Off. . |
| 0 289 479 | 11/1988 | European Pat. Off. . |
| 0 328 383 | 8/1989 | European Pat. Off. . |
| 0 337 604 | 10/1989 | European Pat. Off. . |
| 0 342 633 | 11/1989 | European Pat. Off. . |
| WO 88/08880 | 11/1988 | WIPO . |
| WO 89/01515 | 2/1989 | WIPO . |
| WO 90/09445 | 8/1990 | WIPO . |

OTHER PUBLICATIONS

Sick et al, Nucleic Acids Research, vol. 18, No. 5, p. 1305 (1990).

Herrnstadt et al, Bio/Technology, vol. 4, pp. 305–308 (1986).

Krieg et al, J. Appl. Entomol., vol. 104, No. 4, pp. 417–424 (1987).

Sekar et al, *Proc. Natl. Acad. Sci. USA*, vol. 84, No. 29, pp. 7036–7040 (1987).

Donovan et al, Biosis Database, abstract No. 87–046633 (1987).

*Primary Examiner*—Jean C. Witz

*Attorney, Agent, or Firm*—Burns, Doane, Swecker & Mathis, L.L.P.

[57] ABSTRACT

Two new *Bacillus thuringiensis* strains, which are deposited at the DSM under accession nos. 5131 and 5132, produce crystal proteins during sporulation that are toxic to Coleoptera. The crystal proteins contain 74 kDa and 129 kDa protoxins, respectively, which can yield 68 and 66 kDa toxins, respectively, as trypsin-digestion products. A plant, the genome of which is transformed with a DNA sequence that comes from either one of the strains and that codes for its respective toxin, is resistant to Coleoptera. Each strain, itself, or its crystals, crystal proteins, protoxin or toxin can be used as the active ingredient in an insecticidal composition for combatting Coleoptera.

14 Claims, 24 Drawing Sheets

```
        10         20         30         40         50
TTATCTACAT TTAATCATCT CCATTATAAA TATAATATCT AAACACATTG

        60         70         80         90        100
TTGCAAGAGA ATTAATACTA CTTTGATATT TTTAATATAC TTAACCTAAT

       110        120        130        140        150
GTATTGTTAA GTTAATATAG AAATATACCT ATATTAACAA GGAATTTATT

       160        170        180        190        200
AAAAATAATT TTGTATACTT TTCATTGTAA TAACATGATT TTTAAAACAA

       210        220        230        240        250
AAAAGTGTAT AAACAACTTA TCAGGAAGGG GGGGATGCGC AAAGAATAAA

       260        270        280        290        300
AAGAGAATGC TTATAATGTT CAATGGTTTT ATAGGAAGGC ATTTTATCAG

       310        320        330        340   >
GTAGAAAGTT ATGTATTATG ATAAGAATGG GAGGAAGAAA A ATG
                                              MET

    350         359         368         377
AAT CCA AAC AAT CGA AGT GAA TAT GAT ACG ATA AAG GTT
Asn Pro Asn Asn Arg Ser Glu Tyr Asp Thr Ile Lys Val

386         395         404         413         422
ACA CCT AAC AGT GAA TTG CCA ACT AAC CAT AAT CAA TAT
Thr Pro Asn Ser Glu Leu Pro Thr Asn His Asn Gln Tyr

        431         440         449         458
CCT TTA GCT GAC AAT CCA AAT TCG ACA CTA GAA GAA TTA
Pro Leu Ala Asp Asn Pro Asn Ser Thr Leu Glu Glu Leu
```

FIG. 1A 467 476 485 494
AAT TAT AAA GAA TTT TTA AGA ATG ACT GCA GAC AAT TCT
Asn Tyr Lys Glu Phe Leu Arg MET Thr Ala Asp Asn Ser 503 512↓ 521 530 539
ACG GAA GTG CTA GAC AGC TCT ACA GTA AAA GAT GCA GTT
Thr Glu Val Leu Asp Ser Ser Thr Val Lys Asp Ala Val 548 557 566 575
GGG ACA GGA ATT TCT GTT GTA GGA CAG ATT TTA GGT GTT
Gly Thr Gly Ile Ser Val Val Gly Gln Ile Leu Gly Val 584 593 602 611
GTA GGG GTT CCA TTT GCT GGG GCG CTC ACT TCA TTT TAT
Val Gly Val Pro Phe Ala Gly Ala Leu Thr Ser Phe Tyr 620 629 638 647 656
CAA TCA TTT CTT AAC GCT ATA TGG CCA AGT GAT GCT GAC
Gln Ser Phe Leu Asn Ala Ile Trp Pro Ser Asp Ala Asp 665 674 683 692
CCA TGG AAG GCT TTT ATG GCA CAA GTG GAA GTA CTG ATA
Pro Trp Lys Ala Phe MET Ala Gln Val Glu Val Leu Ile 701 710 719 728
GAT AAG AAA ATA GAG GAG TAT GCT AAA AGT AAA GCT CTT
Asp Lys Lys Ile Glu Glu Tyr Ala Lys Ser Lys Ala Leu 737 746 755 764 773
GCA GAG TTA CAG GGT CTT CAA AAT AAT TTT GAA GAT TAT
Ala Glu Leu Gln Gly Leu Gln Asn Asn Phe Glu Asp Tyr

FIG. 1B 782 791 800 809
GTA AAT GCG TTG GAT TCC TGG AAG AAA GCG CCT GTA AAT
Val Asn Ala Leu Asp Ser Trp Lys Lys Ala Pro Val Asn 818 827 836 845
TTA CGA AGT CGA AGA AGC CAA GAT CGA ATA AGA GAA CTT
Leu Arg Ser Arg Arg Ser Gln Asp Arg Ile Arg Glu Leu 854 863 872 881 890
TTT TCT CAA GCA GAA AGC CAT TTT CGT AAT TCC ATG CCG
Phe Ser Gln Ala Glu Ser His Phe Arg Asn Ser MET Pro 899 908 917 926
TCA TTT GCG GTT TCC AAA TTC GAA GTT CTG TTT CTA CCA
Ser Phe Ala Val Ser Lys Phe Glu Val Leu Phe Leu Pro 935 944 953 962
ACA TAT GCA CAA GCT GCA AAT ACA CAT TTA TTG CTA TTA
Thr Tyr Ala Gln Ala Ala Asn Thr His Leu Leu Leu Leu 971 980 989 998 1007
AAA GAT GCT CAA GTT TTT GGA GAA GAA TGG GGA TAT TCT
Lys Asp Ala Gln Val Phe Gly Glu Glu Trp Gly Tyr Ser 1016 1025 1034 1043
TCA GAA GAT ATT GCT GAA TTT TAT CAA AGA CAA TTA AAA
Ser Glu Asp Ile Ala Glu Phe Tyr Gln Arg Gln Leu Lys 1052 1061 1070 1079
CTT ACG CAA CAA TAC ACT GAC CAT TGT GTC AAT TGG TAT
Leu Thr Gln Gln Tyr Thr Asp His Cys Val Asn Trp Tyr

FIG. 1C 1088 1097 1106 1115 1124
AAT GTT GGA TTA AAT AGT TTA AGA GGT TCA ACT TAT GAT
Asn Val Gly Leu Asn Ser Leu Arg Gly Ser Thr Tyr Asp 1133 1142 1151 1160
GCA TGG GTC AAA TTT AAC CGT TTT CGC AGA GAA ATG ACA
Ala Trp Val Lys Phe Asn Arg Phe Arg Arg Glu MET Thr 1169 1178 1187 1196
TTA ACT GTA TTA GAT CTA ATT GTA TTA TTC CCA TTT TAT
Leu Thr Val Leu Asp Leu Ile Val Leu Phe Pro Phe Tyr 1205 1214 1223 1232 1241
GAT GTT CGG TTA TAC TCA AAA GGA GTT AAA ACA GAA CTA
Asp Val Arg Leu Tyr Ser Lys Gly Val Lys Thr Glu Leu 1250 1259 1268 1277
ACA AGA GAC ATT TTT ACA GAT CCA ATT TTT ACA CTC AAT
Thr Arg Asp Ile Phe Thr Asp Pro Ile Phe Thr Leu Asn 1286 1295 1304 1313
GCT CTT CAA GAG TAT GGA CCA ACT TTT TCG AGT ATA GAA
Ala Leu Gln Glu Tyr Gly Pro Thr Phe Ser Ser Ile Glu 1322 1331 1340 1349 1358
AAC TCT ATT CGA AAA CCT CAT TTA TTT GAT TAT TTG CGT
Asn Ser Ile Arg Lys Pro His Leu Phe Asp Tyr Leu Arg 1367 1376 1385 1394
GGG ATT GAA TTT CAT ACG CGT CTT CGA CCT GGT TAC TCT
Gly Ile Glu Phe His Thr Arg Leu Arg Pro Gly Tyr Ser

FIG. 1D

```
   1403         1412        1421        1430
GGG AAA GAT TCT TTC AAT TAT TGG TCT GGT AAT TAT GTA
Gly Lys Asp Ser Phe Asn Tyr Trp Ser Gly Asn Tyr Val

1439        1448        1457        1466        1475
GAA ACT AGA CCT AGT ATA GGA TCT AAT GAT ACA ATC ACT
Glu Thr Arg Pro Ser Ile Gly Ser Asn Asp Thr Ile Thr

        1484        1493        1502        1511
TCC CCA TTT TAT GGA GAT AAA TCT ATT GAA CCT ATA CAA
Ser Pro Phe Tyr Gly Asp Lys Ser Ile Glu Pro Ile Gln

   1520        1529        1538        1547
AAG CTA AGC TTT GAT GGA CAA AAA GTT TAT CGA ACT ATA
Lys Leu Ser Phe Asp Gly Gln Lys Val Tyr Arg Thr Ile

1556        1565        1574        1583        1592
GCT AAT ACA GAC ATA GCG GCT TTT CCG GAT GGC AAG ATA
Ala Asn Thr Asp Ile Ala Ala Phe Pro Asp Gly Lys Ile

        1601        1610        1619        1628
TAT TTT GGT GTT ACG AAA GTT GAT TTT AGT CAA TAT GAT
Tyr Phe Gly Val Thr Lys Val Asp Phe Ser Gln Tyr Asp

   1637        1646        1655        1664
GAT CAA AAA AAT GAA ACT AGT ACA CAA ACA TAT GAT TCA
Asp Gln Lys Asn Glu Thr Ser Thr Gln Thr Tyr Asp Ser

1673        1682        1691        1700        1709
AAA AGA TAC AAT GGC TAT TTA GGT GCA CAG GAT TCT ATC
Lys Arg Tyr Asn Gly Tyr Leu Gly Ala Gln Asp Ser Ile
```

FIG. 1E

```
        1718        1727        1736        1745
GAC CAA TTA CCA CCA GAA ACA ACA GAT GAA CCA CTT GAA
Asp Gln Leu Pro Pro Glu Thr Thr Asp Glu Pro Leu Glu

     1754        1763        1772        1781
AAA GCA TAT AGT CAT CAG CTT AAT TAC GCA GAA TGT TTC
Lys Ala Tyr Ser His Gln Leu Asn Tyr Ala Glu Cys Phe

1790        1799        1808        1817        1826
TTA ATG CAG GAC CGT CGT GGA ACA ATT CCA TTT TTT ACT
Leu MET Gln Asp Arg Arg Gly Thr Ile Pro Phe Phe Thr

        1835        1844        1853        1862
TGG ACA CAT AGA AGT GTA GAC TTT TTT AAT ACA ATT GAT
Trp Thr His Arg Ser Val Asp Phe Phe Asn Thr Ile Asp

     1871        1880        1889        1898
GCT GAA AAA ATT ACT CAA CTT CCA GTA GTG AAA GCA TAT
Ala Glu Lys Ile Thr Gln Leu Pro Val Val Lys Ala Tyr

1907        1916        1925        1934        1943
GCC TTG TCT TCA GGC GCT TCC ATT ATT GAA GGT CCA GGA
Ala Leu Ser Ser Gly Ala Ser Ile Ile Glu Gly Pro Gly

        1952        1961        1970        1979
TTC ACA GGA GGA AAT TTA CTA TTC CTA AAA GAA TCT AGT
Phe Thr Gly Gly Asn Leu Leu Phe Leu Lys Glu Ser Ser

     1988        1997        2006        2015
AAT TCA ATT GCT AAA TTT AAA GTT ACC TTA AAT TCA GCA
Asn Ser Ile Ala Lys Phe Lys Val Thr Leu Asn Ser Ala
```

FIG. 1F 2024 2033 2042 2051 2060
GCC TTG TTA CAA CGA TAT CGC GTA AGA ATA CGC TAT GCT
Ala Leu Leu Gln Arg Tyr Arg Val Arg Ile Arg Tyr Ala 2069 2078 2087 2096
TCA ACC ACT AAC CTA CGA CTT TTC GTG CAA AAT TCA AAC
Ser Thr Thr Asn Leu Arg Leu Phe Val Gln Asn Ser Asn 2105 2114 2123 2132
AAT GAT TTT CTT GTC ATC TAC ATT AAT AAA ACT ATG AAT
Asn Asp Phe Leu Val Ile Tyr Ile Asn Lys Thr MET Asn 2141 2150 2159 2168 2177
ATA GAT GGT GAT TTA ACA TAT CAA ACA TTT GAT TTC GCA
Ile Asp Gly Asp Leu Thr Tyr Gln Thr Phe Asp Phe Ala 2186 2195 2204 2213
ACT AGT AAT TCT AAT ATG GGA TTC TCT GGT GAT ACA AAT
Thr Ser Asn Ser Asn MET Gly Phe Ser Gly Asp Thr Asn 2222 2231 2240 2249
GAC TTT ATA ATA GGA GCA GAA TCT TTC GTT TCT AAT GAA
Asp Phe Ile Ile Gly Ala Glu Ser Phe Val Ser Asn Glu 2258 2267 2276 2285 2294
AAA ATC TAT ATA GAT AAG ATA GAA TTT ATC CCA GTA CAA
Lys Ile Tyr Ile Asp Lys Ile Glu Phe Ile Pro Val Gln

< 2307 2317 2327 2337 2347
TAG CAAGTGAATT TTGGAATATA GGGCGATGGT CAAAATGAAA GGATAAGAAG

FIG. 1G

```
       2357       2367       2377       2387       2397
GTGAATTTTG ATGGTTAGGA AAGATTCTTT TAACAAAAGC AACATGGAAA

       2407       2417
AGTATACAGT ACAAATGGGT ACCGAGCT
```

FIG. 1H

```
        10         20         30         40         50
TTTGGATTGT GAGCATGTAC AGGTTTGTGA TTTACAAGCA AAACCAATCT

        60         70         80         90        100
GCGAAGATTG TTGTCATTTT ATAAAGGTAA CAGGATATTT TCAAATTTGT

       110        120        130        140        150
ACCGATTAAA TAAAAAATAT TTAGATTAAC ACTGTTGTTT TTTACAACTA

       160        170        180     >  189
TCCGTATGGA CAAATTTAAC AAGGAGTGAA AAT ATG AAT TTA
                                     MET Asn Leu

    198         207         216         225
AAT AAT TTA GAT GGA TAT GAA GAT AGT AAT AGA ACA TTA
Asn Asn Leu Asp Gly Tyr Glu Asp Ser Asn Arg Thr Leu

234         243         252         261         270
AAT AAT TCT CTC AAT TAT CCT ACT CAA AAA GCA TTA TCA
Asn Asn Ser Leu Asn Tyr Pro Thr Gln Lys Ala Leu Ser

        279         288         297         306
CCA TCA TTA AAG AAT ATG AAC TAC CAG GAT TTT TTA TCT
Pro Ser Leu Lys Asn MET Asn Tyr Gln Asp Phe Leu Ser

    315         324         333         342
ATA ACT GAG AGG GAA CAA CCT GAA GCA CTC GCT AGT GGT
Ile Thr Glu Arg Glu Gln Pro Glu Ala Leu Ala Ser Gly

351         360         369         378         387
AAT ACA GCT ATT AAT ACT GTA GTT AGT GTT ACG GGG GCT
Asn Thr Ala Ile Asn Thr Val Val Ser Val Thr Gly Ala
```

FIG. 2A 396 405 414 423
ACA CTA AGT GCG TTA GGT GTC CCA GGT GCA AGT TTT ATC
Thr Leu Ser Ala Leu Gly Val Pro Gly Ala Ser Phe Ile 432 441 450 459
ACT AAC TTT TAC CTG AAA ATT GCA GGC CTT TTA TGG CCA
Thr Asn Phe Tyr Leu Lys Ile Ala Gly Leu Leu Trp Pro 468 477 486 495 504
GAA AAT GGA AAA ATT TGG GAT GAA TTT ATG ACA GAA GTA
Glu Asn Gly Lys Ile Trp Asp Glu Phe MET Thr Glu Val 513 522 531 540
GAA GCA CTT ATT GAT CAA AAA ATA GAA GAA TAT GTA AGA
Glu Ala Leu Ile Asp Gln Lys Ile Glu Glu Tyr Val Arg 549 558 567 576
AAT AAA GCG ATT GCA GAA TTA GAT GGA TTA GGA TCA GCC
Asn Lys Ala Ile Ala Glu Leu Asp Gly Leu Gly Ser Ala 585 594 603 612 621
TTA GAT AAA TAT CAA AAA GCA CTT GCA GAT TGG CTG GGC
Leu Asp Lys Tyr Gln Lys Ala Leu Ala Asp Trp Leu Gly 630 639 648 657
AAA CAA GAT GAT CCA GAA GCT ATA CTT TCT GTG GCA ACT
Lys Gln Asp Asp Pro Glu Ala Ile Leu Ser Val Ala Thr 666 675 684 693
GAA TTT CGT ATA ATA GAT TCT CTT TTT GAA TTT AGT ATG
Glu Phe Arg Ile Ile Asp Ser Leu Phe Glu Phe Ser MET

FIG. 2B

```
702         711         720         729         738
CCT TCA TTT AAG GTT ACT GGA TAT GAA ATA CCA TTA CTA
Pro Ser Phe Lys Val Thr Gly Tyr Glu Ile Pro Leu Leu

        747         756         765         774
ACA GTT TAC GCA CAA GCG GCA AAC CTT CAT CTA GCT TTA
Thr Val Tyr Ala Gln Ala Ala Asn Leu His Leu Ala Leu

    783         792         801         810
TTA AGA GAT TCT ACT CTT TAT GGA GAT AAA TGG GGA TTC
Leu Arg Asp Ser Thr Leu Tyr Gly Asp Lys Trp Gly Phe

819         828         837         846         855
ACT CAG AAC AAC ATT GAG GAA AAT TAT AAT CGT CAA AAG
Thr Gln Asn Asn Ile Glu Glu Asn Tyr Asn Arg Gln Lys

        864         873         882         891
AAA CGC ATT TCT GAA TAT TCA GAC CAT TGC ACC AAG TGG
Lys Arg Ile Ser Glu Tyr Ser Asp His Cys Thr Lys Trp

    900         909         918         927
TAT AAT AGT GGT CTT AGC AGA TTG AAC GGT TCC ACT TAT
Tyr Asn Ser Gly Leu Ser Arg Leu Asn Gly Ser Thr Tyr

936         945         954         963         972
GAA CAA TGG ATA AAT TAT AAT CGT TTT CGT AGA GAA ATG
Glu Gln Trp Ile Asn Tyr Asn Arg Phe Arg Arg Glu MET

        981         990         999         1008
ATA TTA ATG GCA TTA GAT CTT GTC GCT GTA TTT CCT TTT
Ile Leu MET Ala Leu Asp Leu Val Ala Val Phe Pro Phe
```

FIG. 2C 1017 1026 1035 1044
CAT GAC CCT CGA AGG TAT TCA ATG GAA ACA AGT ACG CAG
His Asp Pro Arg Arg Tyr Ser MET Glu Thr Ser Thr Gln 1053 1062 1071 1080 1089
TTA ACG AGA GAA GTG TAT ACC GAT CCA GTT AGC TTG TCA
Leu Thr Arg Glu Val Tyr Thr Asp Pro Val Ser Leu Ser 1098 1107 1116 1125
ATT AGC AAT CCA GAT ATA GGT CCA AGT TTT TCT CAG ATG
Ile Ser Asn Pro Asp Ile Gly Pro Ser Phe Ser Gln MET 1134 1143 1152 1161
GAA AAT ACT GCA ATT AGA ACA CCA CAC CTT GTT GAT TAT
Glu Asn Thr Ala Ile Arg Thr Pro His Leu Val Asp Tyr 1170 1179 1188 1197 1206
TTA GAT GAG CTT TAT ATA TAT ACA TCA AAA TAT AAA GCA
Leu Asp Glu Leu Tyr Ile Tyr Thr Ser Lys Tyr Lys Ala 1215 1224 1233 1242
TTT TCA CAT GAG ATT CAA CCA GAC CTA TTT TAT TGG AGT
Phe Ser His Glu Ile Gln Pro Asp Leu Phe Tyr Trp Ser 1251 1260 1269 1278
GCA CAT AAG GTT AGC TTT AAA AAA TCG GAG CAA TCC AAT
Ala His Lys Val Ser Phe Lys Lys Ser Glu Gln Ser Asn 1287 1296 1305 1314 1323
TTA TAT ACA ACA GGC ATA TAT GGT AAA ACA AGT GGA TAT
Leu Tyr Thr Thr Gly Ile Tyr Gly Lys Thr Ser Gly Tyr

FIG. 2D

```
        1332        1341        1350        1359
ATT TCA TCA GGG GCA TAT TCA TTT CAT GGG AAT GAT ATC
Ile Ser Ser Gly Ala Tyr Ser Phe His Gly Asn Asp Ile

    1368        1377        1386        1395
TAT AGA ACA TTA GCA GCT CCA TCA GTT GTA GTT TAT CCG
Tyr Arg Thr Leu Ala Ala Pro Ser Val Val Val Tyr Pro

1404        1413        1422        1431        1440
TAT ACT CAG AAT TAT GGT GTC GAG CAA GTT GAG TTT TAC
Tyr Thr Gln Asn Tyr Gly Val Glu Gln Val Glu Phe Tyr

        1449        1458        1467        1476
GGT GTA AAA GGG CAT GTA CAT TAT AGA GGA GAT AAC AAA
Gly Val Lys Gly His Val His Tyr Arg Gly Asp Asn Lys

    1485        1494        1503        1512
TAT GAT CTG ACG TAT GAT TCT ATT GAT CAA TTA CCC CCA
Tyr Asp Leu Thr Tyr Asp Ser Ile Asp Gln Leu Pro Pro

1521        1530        1539        1548        1557
GAC GGA GAA CCA ATA CAC GAA AAA TAC ACT CAT CGA TTA
Asp Gly Glu Pro Ile His Glu Lys Tyr Thr His Arg Leu

        1566        1575        1584        1593
TGT CAT GCT ACA GCT ATA TTT AAA TCA ACT CCG GAT TAT
Cys His Ala Thr Ala Ile Phe Lys Ser Thr Pro Asp Tyr

    1602        1611        1620        1629
GAT AAT GCT ACT ATC CCG ATC TTT TCT TGG ACG CAT AGA
Asp Asn Ala Thr Ile Pro Ile Phe Ser Trp Thr His Arg
```

FIG. 2E 1638 1647 1656 1665 1674
AGT GCG GAG TAT TAC AAT AGA ATC TAT CCA AAC AAA ATC
Ser Ala Glu Tyr Tyr Asn Arg Ile Tyr Pro Asn Lys Ile 1683 1692 1701 1710
ACA AAA ATT CCA GCT GTA AAA ATG TAT AAA CTA GAT GAT
Thr Lys Ile Pro Ala Val Lys MET Tyr Lys Leu Asp Asp 1719 1728 1737 1746
CCA TCT ACA GTT GTC AAA GGG CCT GGA TTT ACA GGT GGA
Pro Ser Thr Val Val Lys Gly Pro Gly Phe Thr Gly Gly 1755 1764 1773 1782 1791
GAT TTA GTT AAG AGA GGG AGT ACT GGT TAT ATA GGA GAT
Asp Leu Val Lys Arg Gly Ser Thr Gly Tyr Ile Gly Asp 1800 1809 1818 1827
ATA AAG GCT ACC GTA AAC TCT CCA CTT TCT CAA AAA TAT
Ile Lys Ala Thr Val Asn Ser Pro Leu Ser Gln Lys Tyr 1836 1845 1854 1863
CGT GTT AGA GTT CGA TAC GCT ACT AAT GTT TCT GGA CAA
Arg Val Arg Val Arg Tyr Ala Thr Asn Val Ser Gly Gln 1872 1881 1890 1899 1908
TTC AAC GTG TAT ATT AAT GAT AAA ATA ACG CTT CAA ACA
Phe Asn Val Tyr Ile Asn Asp Lys Ile Thr Leu Gln Thr 1917 1926 1935 1944
AAG TTT CAA AAT ACT GTA GAA ACA ATA GGT GAA GGA AAA
Lys Phe Gln Asn Thr Val Glu Thr Ile Gly Glu Gly Lys

FIG. 2F 1953 1962 1971 1980
GAT TTA ACC TAT GGT TCA TTT GGA TAT ATA GAA TAT TCT
Asp Leu Thr Tyr Gly Ser Phe Gly Tyr Ile Glu Tyr Ser 1989 1998 2007 2016 2025
ACG ACC ATT CAA TTT CCG GAT GAG CAT CCA AAA ATC ACT
Thr Thr Ile Gln Phe Pro Asp Glu His Pro Lys Ile Thr 2034 2043 2052 2061
CTT CAT TTA AGC GAT TTG AGT AAC AAT TCA TCA TTT TAT
Leu His Leu Ser Asp Leu Ser Asn Asn Ser Ser Phe Tyr 2070 2079 2088 2097
GTA GAT TCA ATC GAA TTT ATC CCT GTA GAT GTA AAT TAT
Val Asp Ser Ile Glu Phe Ile Pro Val Asp Val Asn Tyr 2106 2115 2124 2133 2142
GCT GAA AAA GAA AAA CTA GAA AAA GCA CAG AAA GCC GTG
Ala Glu Lys Glu Lys Leu Glu Lys Ala Gln Lys Ala Val 2151 2160 2169 2178
AAT ACC TTG TTT ACA GAG GGA AGA AAT GCA CTC CAA AAA
Asn Thr Leu Phe Thr Glu Gly Arg Asn Ala Leu Gln Lys 2187 2196 2205 2214
GAC GTG ACA GAT TAT AAA GTG GAC CAG GTT TCA ATT TTA
Asp Val Thr Asp Tyr Lys Val Asp Gln Val Ser Ile Leu 2223 2232 2241 2250 2259
GTG GAT TGT ATA TCA GGG GAT TTA TAT CCC AAT GAG AAA
Val Asp Cys Ile Ser Gly Asp Leu Tyr Pro Asn Glu Lys

FIG. 2G 2268 2277 2286 2295
CGC GAA CTA CAA AAT CTA GTC AAA TAC GCA AAA CGT TTG
Arg Glu Leu Gln Asn Leu Val Lys Tyr Ala Lys Arg Leu 2304 2313 2322 2331
AGC TAT TCC CGT AAT TTA CTT CTA GAT CCA ACA TTC GAT
Ser Tyr Ser Arg Asn Leu Leu Leu Asp Pro Thr Phe Asp 2340 2349 2358 2367 2376
TCT ATT AAT TCA TCT GAG GAG AAT GGT TGG TAT GGA AGT
Ser Ile Asn Ser Ser Glu Glu Asn Gly Trp Tyr Gly Ser 2385 2394 2403 2412
AAT GGT ATT GTG ATT GGA AAT GGG GAT TTT GTA TTC AAA
Asn Gly Ile Val Ile Gly Asn Gly Asp Phe Val Phe Lys 2421 2430 2439 2448
GGT AAC TAT TTA ATT TTT TCA GGT ACC AAT GAT ACA CAA
Gly Asn Tyr Leu Ile Phe Ser Gly Thr Asn Asp Thr Gln 2457 2466 2475 2484 2493
TAT CCA ACA TAT CTC TAC CAA AAA ATA GAT GAA TCC AAA
Tyr Pro Thr Tyr Leu Tyr Gln Lys Ile Asp Glu Ser Lys 2502 2511 2520 2529
CTC AAA GAA TAT ACA CGC TAT AAA CTG AAA GGT TTT ATC
Leu Lys Glu Tyr Thr Arg Tyr Lys Leu Lys Gly Phe Ile 2538 2547 2556 2565
GAA AGT AGT CAG GAT TTA GAA GCT TAT GTG ATT CGC TAT
Glu Ser Ser Gln Asp Leu Glu Ala Tyr Val Ile Arg Tyr

FIG. 2H

```
2574        2583        2592        2601        2610
 GAT GCA AAA CAT AGA ACA TTG GAT GTT TCT GAT AAT CTA
 Asp Ala Lys His Arg Thr Leu Asp Val Ser Asp Asn Leu

         2619        2628        2637        2646
 TTA CCA GAT ATT CTC CCT GAG AAT ACA TGT GGA GAA CCA
 Leu Pro Asp Ile Leu Pro Glu Asn Thr Cys Gly Glu Pro

     2655        2664        2673        2682
 AAT CGC TGC GCG GCA CAA CAA TAC CTG GAT GAA AAT CCA
 Asn Arg Cys Ala Ala Gln Gln Tyr Leu Asp Glu Asn Pro

2691        2700        2709        2718        2727
 AGT CCA GAA TGT AGT TCG ATG CAA GAT GGA ATT TTG TCT
 Ser Pro Glu Cys Ser Ser MET Gln Asp Gly Ile Leu Ser

         2736        2745        2754        2763
 GAT TCG CAT TCA TTT TCT CTT AAT ATA GAT ACA GGT TCT
 Asp Ser His Ser Phe Ser Leu Asn Ile Asp Thr Gly Ser

     2772        2781        2790        2799
 ATC AAT CAC AAT GAG AAT TTA GGA ATT TGG GTG TTG TTT
 Ile Asn His Asn Glu Asn Leu Gly Ile Trp Val Leu Phe

2808        2817        2826        2835        2844
 AAA ATT TCG ACA TTA GAA GGA TAT GCG AAA TTT GGA AAT
 Lys Ile Ser Thr Leu Glu Gly Tyr Ala Lys Phe Gly Asn

         2853        2862        2871        2880
 CTA GAA GTG ATT GAA GAT GGC CCA GTT ATT GGA GAA GCA
 Leu Glu Val Ile Glu Asp Gly Pro Val Ile Gly Glu Ala
```

FIG. 2I 2889 2898 2907 2916
TTA GCC CGT GTG AAA CGC CAA GAA ACG AAG TGG AGA AAC
Leu Ala Arg Val Lys Arg Gln Glu Thr Lys Trp Arg Asn 2925 2934 2943 2952 2961
AAG TTA GCC CAA CTG ACA ACG GAA ACA CAA GCG ATT TAT
Lys Leu Ala Gln Leu Thr Thr Glu Thr Gln Ala Ile Tyr 2970 2979 2988 2997
ACA CGA GCA AAA CAA GCG CTG GAT AAT CTT TTT GCG AAT
Thr Arg Ala Lys Gln Ala Leu Asp Asn Leu Phe Ala Asn 3006 3015 3024 3033
GCA CAA GAC TCT CAC TTA AAA AGA GAT GTT ACA TTT GCG
Ala Gln Asp Ser His Leu Lys Arg Asp Val Thr Phe Ala 3042 3051 3060 3069 3078
GAA ATT GCG GCT GCA AGA AAG ATT GTC CAA TCA ATA CGC
Glu Ile Ala Ala Ala Arg Lys Ile Val Gln Ser Ile Arg 3087 3096 3105 3114
GAA GCG TAT ATG TCA TGG TTA TCT GTT GTT CCA GGT GTA
Glu Ala Tyr MET Ser Trp Leu Ser Val Val Pro Gly Val 3123 3132 3141 3150
AAT CAC CCT ATT TTT ACA GAG TTA AGT GGG CGA GTA CAA
Asn His Pro Ile Phe Thr Glu Leu Ser Gly Arg Val Gln 3159 3168 3177 3186 3195
CGA GCA TTT CAA TTA TAT GAT GTA CGA AAT GTT GTG CGT
Arg Ala Phe Gln Leu Tyr Asp Val Arg Asn Val Val Arg

FIG. 2J 3204 3213 3222 3231
AAT GGT CGA TTC CTC AAT GGC TTA TCC GAT TGG ATT GTA
Asn Gly Arg Phe Leu Asn Gly Leu Ser Asp Trp Ile Val 3240 3249 3258 3267
ACA TCT GAC GTA AAG GTA CAA GAA GAA AAT GGG AAT AAC
Thr Ser Asp Val Lys Val Gln Glu Glu Asn Gly Asn Asn 3276 3285 3294 3303 3312
GTA TTA GTT CTT AAC AAT TGG GAT GCA CAA GTA TTA CAA
Val Leu Val Leu Asn Asn Trp Asp Ala Gln Val Leu Gln 3321 3330 3339 3348
AAC GTA AAA CTC TAT CAA GAC CGT GGG TAT ATC TTA CAT
Asn Val Lys Leu Tyr Gln Asp Arg Gly Tyr Ile Leu His 3357 3366 3375 3384
GTA ACA GCG CGC AAG ATA GGA ATT GGG GAA GGA TAT ATA
Val Thr Ala Arg Lys Ile Gly Ile Gly Glu Gly Tyr Ile 3393 3402 3411 3420 3429
ACG ATT ACG GAT GAA GAA GGG CAT ACA GAT CAA TTG AGA
Thr Ile Thr Asp Glu Glu Gly His Thr Asp Gln Leu Arg 3438 3447 3456 3465
TTT ACT GCA TGT GAA GAG ATT GAT GCA TCT AAT GCG TTT
Phe Thr Ala Cys Glu Glu Ile Asp Ala Ser Asn Ala Phe 3474 3483 3492 3501
ATA TCC GGT TAT ATT ACA AAA GAA CTG GAA TTC TTC CCA
Ile Ser Gly Tyr Ile Thr Lys Glu Leu Glu Phe Phe Pro

FIG. 2K

```
3510        3519        3528        3537        3546
GAT ACA GAG AAA GTG CAT ATA GAA ATA GGC GAA ACA GAA
Asp Thr Glu Lys Val His Ile Glu Ile Gly Glu Thr Glu

        3555        3564        3573        3582
GGA ATA TTC CTG GTA GAA AGT ATA GAG TTA TTT TTG ATG
Gly Ile Phe Leu Val Glu Ser Ile Glu Leu Phe Leu MET

    3591        3600 <      3610       3620       3630
GAA GAG CTA TGT TAA TAGGGAGATT ATTCAACAAA TATTTGTTTG
Glu Glu Leu Cys

      3640       3650       3660       3670       3680
ATTCAAAATA AAATAAAATG CATACAATCC TCTTTATCAG ACGGTATTTC

      3690       3700       3710       3720       3730
TAATAATTAT AAATATAGGT TGAAAGTTAA AAAATAAAAA CACGCTATTC

      3740       3750       3760       3770       3780
CCATTACTAG AAGGAGGGAG TAACGTGTTT TTTCATGAGT AAAAAAACAA

      3790       3800       3810       3820       3830
TTAGCTATAT TTATCTATTC TCTATAGAAG AAGCGGATTG ATAAGAACCG

      3840       3850       3860       3870       3880
TAAGTGACAG GAATAGCATT TATATCTTAT AGTGCAAGTC CAAACAAATG

      3890       3900       3910       3920       3930
AGGGTAGTAG AGTGACAAAA ACGCTTGAAG TTTTCCAAAA AAGAAATCAA

      3940       3950       3960       3970       3980
GTACAAATTG AAATTAGTAC AACAAATGTT ATTTCTTTAG TAGAACGTAT
```

FIG. 2L

```
3990       4000
AGAATTATTA TGTTTGGAAG ATGA
```

FIG. 2M

*BACILLUS THURINGIENSIS* INSECTICIDAL TOXINS

This application is a continuation of application Ser. No. 08/247,459, filed May 23, 1994 now abandoned, which is a continuation of application Ser. No. 07/741,440, filed Aug. 6, 1991, now abandoned.

This invention relates to two new strains of *B. thuringiensis* (the "BtPGSI208 strain" and the "BtPGSI245 strain"), each of which produces crystallized proteins (the "BtPGSI208 crystal proteins" and the "BtPGSI245 crystal proteins", respectively) which are packaged in crystals (the "BtPGSI208 crystals" and the "BtPGSI245 crystals", respectively) during sporulation. The BtPGSI208 and BtPGSI245 strains were deposited under the provisions of the Budapest Treaty at the Deutsche Sammlung Für Mikroorganismen and Zellkulturen ("DSM"), Mascheroder Weg 1B, D-3300 Braunschweig, Federal Republic of Germany, under accession numbers 5131 and 5132, respectively, on Jan. 19, 1989.

This invention also relates to an insecticide composition that is active against Coleoptera and that comprises the BtPGSI208 or BtPGSI245 strain, as such, or preferably the BtPGSI208 or BtPGSI245 crystals, crystal proteins or the active component(s) ingredient.

This invention further relates to:

1) a DNA sequence (the "btPGSI208 gene"), from the genome of the BtPGSI208 strain, which encodes a 74 kDa protein (the "BtPGSI208 protoxin") that is found in the BtPGSI208 crystals; and
2) A DNA sequence (the "btPGSI245 gene), from the genome of the BtPGSI245 strain, which encodes a 129 kDa protein (the "BtPGSI245 protoxin") that is found in the BtPGSI245 crystals.

The BtPGSI208 and BtPGSI245 protoxins are the proteins that are produced by their respective BtPGSI208 and BtPGSI245, strains before being packaged into their respective BtPGSI208 and BtPGSI245 crystals.

This invention still further relates to a 68 kDa protein ("the BtPGSI208 toxin") and a 66 kDa protein (the "BtPGSI245 toxin") which can be obtained (e.g., by trypsin digestion) from the BtPGSI208 protoxin and the BtPGSI245 protoxin, respectively. The BtPGSI208 and BtPGSI245 toxins are insecticidally active proteins which can be liberated from the BtPGSI208 crystals and the BtPGSI245 crystals, respectively, produced by the BtPGSI208 strain and the BtPGSI245 strain, respectively, and each toxin has a high activity against Coleoptera. The BtPGSI208 and BtPGSI245 toxins are believed to represent the smallest portions of their respective BtPGSI208 and BtPGSI245 protoxins which are insecticidally effective against Coleoptera.

This invention yet further relates to a chimaeric gene that can be used to transform a plant cell and that contains:

1) a part of the btPGSI208 or btPGSI245 gene (the "insecticidally effective btPGSI208 or btPGSI245 gene part") encoding an insectidicidally effective portion of the respective BtPGSI208 or BtPGSI245 protoxin, preferably a truncated part of the btPGSI208 or btPGSI245 gene (the "truncated btPGSI208 or btPGSI245 gene") encoding just the respective BtPGSI208 or BtPGSI245 toxin;
2) a promoter suitable for transcription of the insecticidally effective btPGSI208 or btPGSI245 gene part in a plant cell; and
3 ) suitable transcription termination and polyadenylation signals for expressing the insecticidally effective btPGSI208 or btPGSI245 gene part in a plant cell.

This chimaeric gene is hereinafter generally referred to as the "btPGSI208 or btPGSI245 chimaeric gene." Preferably, the insecticidally effective btPGSI208 or btPGSI245 gene part is present in the btPGSI208 or btPGSI245 chimaeric gene as a hybrid gene comprising a fusion of the truncated btPGSI208 or btPGSI245 gene and a selectable marker gene, such as the neo gene (the "btPGSI208-neo or btPGSI245-neo hybrid gene") encoding a BtPGSI208-NPTII or BtPGSI245-NPTII fusion protein.

This invention also relates to:

1) a cell (the "transformed plant cell") of a plant, such as potato, the genome of which is transformed with the insecticidally effective btPGSI208 or btPGSI245 gene part; and
2) a plant (the "transformed plant") which is regenerated from the transformed plant cell or is produced from the so-regenerated plant, the genome of which contains the insecticidally effective btPGSI208 or btPGSI245 gene part and which is resistant to Coleoptera.

This invention still further relates to a *B. thuringiensis* ("Bt") strain transformed, preferably by electroporation, with a vector carrying all or part of the btPGSI208 or btPGSI245 gene.

BACKGROUND OF THE INVENTION

*B. thuringiensis* is a gram-positive bacterium which produces endogenous crystals upon sporulation. The crystals are composed of proteins which are specifically toxic against insect larvae. Three different Bt pathotypes have been described: pathotype A that is active against Lepidoptera, e.g., caterpillars; pathotype B that is active against certain Diptera, e.g., mosquitos and black flies; and pathotype C that is active against Coleoptera, e.g., beetles (Ellar et al, 1986).

A Bt strain, whose crystals are toxic to Coleoptera, has been described as *Bt tenebrionis* (U.S. Pat. No. 4,766,203; European patent publication 0,149,162), Bt M-7 or Bt San Diego (European patent publication 0,213,818; U.S. Pat. No. 4,771,131) and BtS1 (European patent application 88/402,115.5).

The fact that conventional submerged fermentation techniques can be used to produce Bt spores on a large scale makes Bt bacteria commercially attractive as a source of insecticidal compositions.

Gene fragments from some Bt strains, encoding insecticidal proteins, have heretofore been identified and integrated into plant genomes in order to render the plants insect-resistant. However, obtaining expression of such Bt gene fragments in plants is not a straightforward process. To achieve optimal expression of an insecticidal protein in plant cells, it has been found necessary to engineer each Bt gene fragment in a specific way so that it encodes a water-soluble part of a Bt protoxin that retains substantial toxicity against its target insects (European patent applications 86/300,291.1 and 88/402,115.5; U.S. patent application Ser. No. 821,582, filed Jan. 22, 1986)

SUMMARY OF THE INVENTION

In accordance with this invention, the two new Bt strains of pathotype C, i.e., the BtPGSI208 and BtPGSI245 strains, are provided. The BtPGSI208 and BtPGSI245 crystals, crystal proteins, protoxins and toxins, produced by the respective strains during sporulation, as well as insecticidally effective portions of the BtPGSI208 and BtPGSI245 protoxins, each possess insecticidal activity and can therefore be formulated into insecticidal compositions against Coleoptera in general, especially against *Agelastica alni*,

*Diabrotica luteola, Haltica tombacina, Anthonomus grandis, Tenebrio molitor, Diabrotica undecimpunctata* and *Triboleum castaneum* and particularly against the Colorado potato beetle, *Leptinotarsa decemlineata*, which is a major pest of economically important crops.

Also in accordance with this invention, a plant cell genome is transformed with the insecticidally effective btPGSI208 or btPGSI245 gene part, preferably the truncated btPGSI208 or btPGSI245 gene. It is preferred that this transformation be carried with the btPGSI208 or btPGSI245 chimaeric gene. The resulting transformed plant cell can be used to produce a transformed plant in which the plant cells in some or all of the plant tissues: 1) contain the insecticidally effective btPGSI208 or btPGSI245 gene part as a stable insert in their genome and 2) express the insecticidally effective btPGSI208 or btPGSI245 gene part by producing an insecticidally effective portion of its respective BtPGSI208 or BtPGSI245 protoxin, preferably its respective BtPGSI208 or BtPGSI245 toxin, thereby rendering the plant resistant to Coleoptera. The transformed plant cells of this invention can also be used to produce, for recovery, such insecticidal Bt proteins.

Further in accordance with this invention, a process is provided for rendering a plant resistant to Coleoptera by transforming the plant cell genome with the insecticidally effective btPGSI208 or btPGSI245 gene part, preferably the truncated btPGSI208 or btPGSI245 gene. In this regard, it is preferred that the plant cell be transformed with the btPGSI208 or btPGSI245 chimaeric gene.

Still further in accordance with this invention, there are provided the BtPGSI208 and BtPGSI245 protoxins, the insecticidally effective portions of such protoxins and the BtPGSI208 and BtPGSI245 toxins, as well as the btPGSI208 and btPGSI245 genes, the insecticidally effective btPGSI208 and btPGSI245 gene parts, the truncated btPGSI208 and btPGSI245 genes and the chimaeric btPGSI208 and btPGSI245 genes.

Yet further in accordance with this invention, a Bt strain is transformed, preferably by electroporation, with a vector carrying all or part of the btPGSI208 or btPGSI245 gene encoding all or an insecticidally effective portion of the BtPGSI208 or BtPGSI245 protoxin.

DETAILED DESCRIPTION OF THE INVENTION

In accordance with this invention, the BtPGSI208 and BtPGSI245 protoxins can be isolated in a conventional manner from, respectively, the BtPGSI208 strain, deposited at the DSM under accession number 5131, and the BtPGSI245 strain, deposited at the DSM under accession number 5132. For example, the BtPGSI208 and BtPGSI245 crystals can be isolated from sporulated cultures of their respective strains (Mahillon and Delcour, 1984), and then, the respective protoxins can be isolated from these crystals according to the method of Höfte et al (1986). The protoxins can be used to prepare monoclonal or polyclonal antibodies specific for these protoxins in a conventional manner (H öfte et al, 1988). The BtPGSI208 toxin can then be obtained by removing (e.g., by trypsin digestion) approximately 57 N-terminal amino acids from the BtPGSI208 protoxin. The BtPGSI245 toxin can be obtained by removing (e.g., by trypsin digestion) approximately 52 N-terminal and approximately 501 C-terminal amino acids from the BtPGSI245 protoxin.

The btPGSI208 and btPGSI245 genes can also be isolated from their respective strains in a conventional manner. For example, the btPGSI208 or btPGSI245 gene can be identified in its respective BtPGSI208 or BtPGSI245 strain, using the procedure described in U.S. patent application Ser. No. 821,582, filed Jan. 22, 1986, and in European patent applications 86/300,291.1 and 88/402,115.5 (which are incorporated herein by reference). Preferably, the btPGSI208 and btPGSI245 genes are each identified by: digesting total DNA from their respective BtPGSI208 and BtPGSI245 strains with one or more restriction enzymes; size fractionating the DNA fragments, so produced, into DNA fractions of 5 to 10 Kb; ligating such fractions to cloning vectors; transforming *E. coli* with the cloning vectors; and screening the clones with a suitable DNA probe. The DNA probe can be constructed: 1) from a highly conserved region of a Bt gene which codes for another crystal protoxin against Coleoptera such as: the bt13 gene described in European patent application 88/402,115.5 and by Höfte et al (1987); or 2) on the basis of the N-terminal amino acid sequence of the protoxin encoded by the respective btPGSI208 or btPGSI245 gene, which sequence can be determined by gas-phase sequencing of the immobilized protoxin (European Patent application 88/402,115.5).

Alternatively, the 5 to 10 kB fragments, prepared from total DNA of the BtPGSI208 or BtPGSI245 strain, can be ligated in suitable expression vectors and transformed in *E. coli*, and the clones can then be screened by conventional colony immunoprobing methods (French et al, 1986) for expression of the BtPGSI208 or BtPGSI245 toxin with monoclonal or polyclonal antibodies raised against the toxin.

The so-identifed btPGSI208 and btPGSI245 genes can then each be sequenced in a conventional manner (Maxam and Gilbert, 1980) to obtain the DNA sequences shown in FIGS. 1 and 2, respectively. The nucleotide sequences of the btPGSI208 gene and btPGSI245 gene, shown in FIGS. 1 and 2, prove that the BtPGSI208 and BtPGSI245 protoxins and toxins are different from previously described protoxins and toxins with activity against Coleoptera (Höfte and Whiteley, 1989).

An insecticidally effective part of each of the sequenced genes, encoding an insecticidally effective portion of its protoxin, and a truncated part of each of the sequenced genes, encoding just its toxin, can be made in a conventional manner from each gene after the gene has been sequenced. The aminoacid sequences of the BtPGSI208 and BtPGSI245 protoxins and toxins can be determined from the DNA sequences of their respective btPGSI208 and btPGSI245 genes and truncated btPGSI208 and btPGSI245 genes. By "an insecticidally effective part" or "a part" of the btPGSI208 or btPGSI245 gene is meant a DNA sequence encoding a polypeptide which has fewer amino acids then the respective BtPGSI208 or BtPGSI245 protoxin but which is still toxic to Coleoptera. Such a part of the btPGSI208 or btPGSI245 gene can encode a BtPGSI208 or BtPGSI245 protoxin which has been truncated towards at least one trypsin cleavage site of the protoxin (U.S. patent application Ser. No. 821,582; European patent application 86/300291.1).

In order to express all or an insecticidally effective part of the btPGSI208 or btPGSI245 gene in *E. coli* and in plants, suitable restriction sites are introduced, flanking each gene or gene part. This can be done by site directed mutagenesis, using well-known procedures (Stanssens et al, 1987; Stanssens et al, 1989).

The insecticidally effective btPGSI208 or btPGSI245 gene part, encoding an insecticidally effective portion of its respective BtPGSI208 or BtPGSI245 protoxin, can be stably inserted in a conventional manner into the nuclear genome of a single plant cell, and the so-transformed plant cell be used in a conventional manner to produce a transformed plant that is insect-resistant. In this regard, a disarmed Ti-plasmid, containing the insectidicidally effective btPGSI208 or btPGSI245 gene part, in *Agrobacterium tumefaciens* can be used to transform the plant cell, and thereafter, a transformed plant can be regenerated from the transformed plant cell using the procedures described, for example, in European patent publications 0,116,718 and 0,270,822, PCT publication WO 84/02,913 and European patent application 87/400,544.0 (which are also incorporated herein by reference).

The resulting transformed plant can be used in a conventional plant breeding scheme to produce more transformed plants with the same characteristics or to introduce the insecticidally effective btPGSI208 or btPGSI245 gene part in other varieties of the same or related plant species. Seeds, which are obtained from the transformed plants, contain the insecticidally effective btPGSI208 or btPGSI245 gene part as a stable genomic insert. Cells of the transformed plant can be cultured in a conventional manner to produce the BtPGSI208 or BtPGSI245 protoxin, preferably the respective toxin, which can be recovered for use in conventional insecticide compositions against Coleoptera (U.S. patent application Ser. No. 821,582; European patent application 86/300291.1.).

The insecticidally effective btPGSI208 or btPGSI245 gene part, preferably the truncated btPGSI208 or btPGSI245 gene, is inserted in a plant cell genome so that the inserted part of the gene is downstream (i.e., 3') of, and under the control of, a promoter which can direct the expression of the gene part in the plant cell. This is preferably accomplished by inserting the btPGSI208 or btPGSI245 chimaeric gene in the plant cell genome. Preferred promoters include: the strong constitutive 35S promoters (the "35S promoters") of the cauliflower mosaic virus of isolates CM 1841 (Gardner et al, 1981), CabbB-S (Franck et al, 1980) and CabbB-JI (Hull and Howell, 1987); and the TR1' promoter and the TR2' promoter (the "TR1' promoter" and "TR2' promoter", respectively) which drive the expression of the 1' and 2' genes, respectively, of the T-DNA (Velten et al, 1984). Alternatively, a promoter can be utilized which is not constitutive but rather is specific for one or more tissues or organs of the plant (e.g., leaves and/or roots) whereby the inserted btPGSI208 or btPGSI245 gene part is expressed only in cells of the specific tissue(s) or organ(s). For example, the btPGSI208 or btPGSI245 gene part could be selectively expressed in the leaves of a plant (e.g., potato) by placing the gene part under the control of a light-inducible promoter such as the promoter of the ribulose-1,5-bisphosphate carboxylase small subunit gene of the plant itself or of another plant such as pea as disclosed in U.S. patent application Ser. No. 821,582 and European patent application 86/300,291.1. Another alternative is to use a promoter whose expression is inducible (e.g., by temperature or chemical factors).

The insecticidally effective btPGSI208 or btPGSI245 gene part is inserted in the plant genome so that the inserted part of the gene is upstream (i.e., 5') of suitable 3' transcription regulation signals (i.e., transcription termination and polyadenylation signals). This is preferably accomplished by inserting the btPGSI208 or btPGSI245 chimaeric gene in the plant cell genome. Preferred polyadenylation and transcription termination signals include those of the octopine synthase gene (Gielen et al, 1984) and the T-DNA gene 7 (Velten and Schell, 1985), which act as 3'-untranslated DNA sequences in transformed plant cells.

It is preferred that the insecticidally effective btPGSI208 or btPGSI245 gene part be inserted in the plant genome in the same transcriptional unit as, and under the control of, the same promoter as a selectable marker gene. The resulting hybrid btPGSI208 or btPGSI245-marker gene will, thereby, be expressed in a transformed plant as a fusion protein (U.S. patent application Ser. No. 821,582; European patent application 86/300291.1; Vaeck et al, 1987). This result is preferably accomplished by inserting a btPGSI208 or btPGSI245 chimaeric gene, containing the marker gene, in the plant cell genome. Any conventional marker gene can be utilized, the expression of which can be used to select transformed plant cells. An example of a suitable selectable marker gene is an antibiotic resistance gene such as the neo gene coding for kanamycin resistance (Reiss et al, 1984; European patent application 87/400,544.0; U.S. patent application Ser. No. 821,582; European patent application 86/300,291.1). Thereby, the insecticidally effective btPGSI208 or btPGSI245 gene part and the marker gene (e.g. the btPGSI208-neo or btPGSI245-neo hybrid gene) are expressed in a transformed plant as a fusion protein (U.S. patent application Ser. No. 821,582; European patent application 86/300,291.1; Vaeck et al, 1987).

All or part of the btPGSI208 and btPGSI245 genes, encoding Coleopteran toxins, can also be used to transform gram-positive bacteria, such as a *B. thuringiensis* which has insecticidal activity against Lepidoptera or Coleoptera. Thereby, a transformed Bt strain can be produced which useful for combatting both Lepidopteran and Coleopteran insect pests or combatting additional Coleopteran insect pests. Transformation of a bacteria with all or part of the btPGSI208 or btPGSI245 gene, incorporated in a suitable cloning vehicle, can be carried out in a conventional manner, preferably using conventional electroporation techniques as described in PCT patent application PCT/EP89/01539, filed Dec. 11, 1989.

Each of the BtPGSI208 and BtPGSI245 strains can be fermented by conventional methods (Dulmage, 1981) to provide high yields of cells. Under appropriate conditions which are well understood (Dulmage, 1981), the BtPGSI208 and BtPGSI245 strains each sporulate to provide their respective BtPGSI208 and BtPGSI245 crystal proteins in high yields.

An insecticide composition of this invention can be formulated in a conventional manner using the BtPGSI208 or BtPGSI245 strain or preferably their respective crystals, crystal proteins, protoxin, toxin and/or insecticidally effective portions of their respective protoxin as active ingredient (s), together with suitable carriers, diluents, emulsifiers and/or dispersants. This insecticide composition can be formulated as a wettable powder, pellets, granules or a dust or as a liquid formulation with aqueous or non-aqueous solvents as a foam, gel, suspension, concentrate, etc. The concentration of the BtPGSI208 or BtPGSI245 strain, crystals, crystal proteins, protoxin, toxin and/or protoxin portions in such a composition will depend upon the nature of the formulation and its intended mode of use. Generally, an insecticide composition of this invention can be used to protect a potato field for 2 to 4 weeks against Coleoptera with each application of the composition. For more extended protection (e.g., for a whole growing season), additional amounts of the composition should be applied periodically.

BRIEF DESCRIPTION OF THE DRAWINGS

The following Examples illustrate the invention. The figures, referred to in the Examples, are as follows:

FIG. 1—DNA sequence of the btPGSI208 gene. The derived aminoacid sequence of the encoded BtPGSI208 protoxin is presented beneath this sequence. The arrow separates the N-terminal 57 aminoacids from the C-terminal portions encoding the BtPGSI208 toxin. The truncated btPGSI208 gene, coding just for the BtPGSI208 toxin, extends from nucleotide position 513 (see arrow) to the TAG termination codon at nucleotide position 2295.

FIG. 2—DNA sequence of the btPGSI245 gene. The derived aminoacid sequence of the encoded BtPGSI245 protoxin is presented beneath this sequence. The arrows delineate the BtPGSI245 toxin between aminoacids 52 and 638 of the BtPGSI245 protoxin. The truncated btPGSI245 gene, coding just for the BtPGSI245 gene, extends from nucleotide position 340 (see arrow) to nucleotide position 2094 (see arrow).

Figure 3:
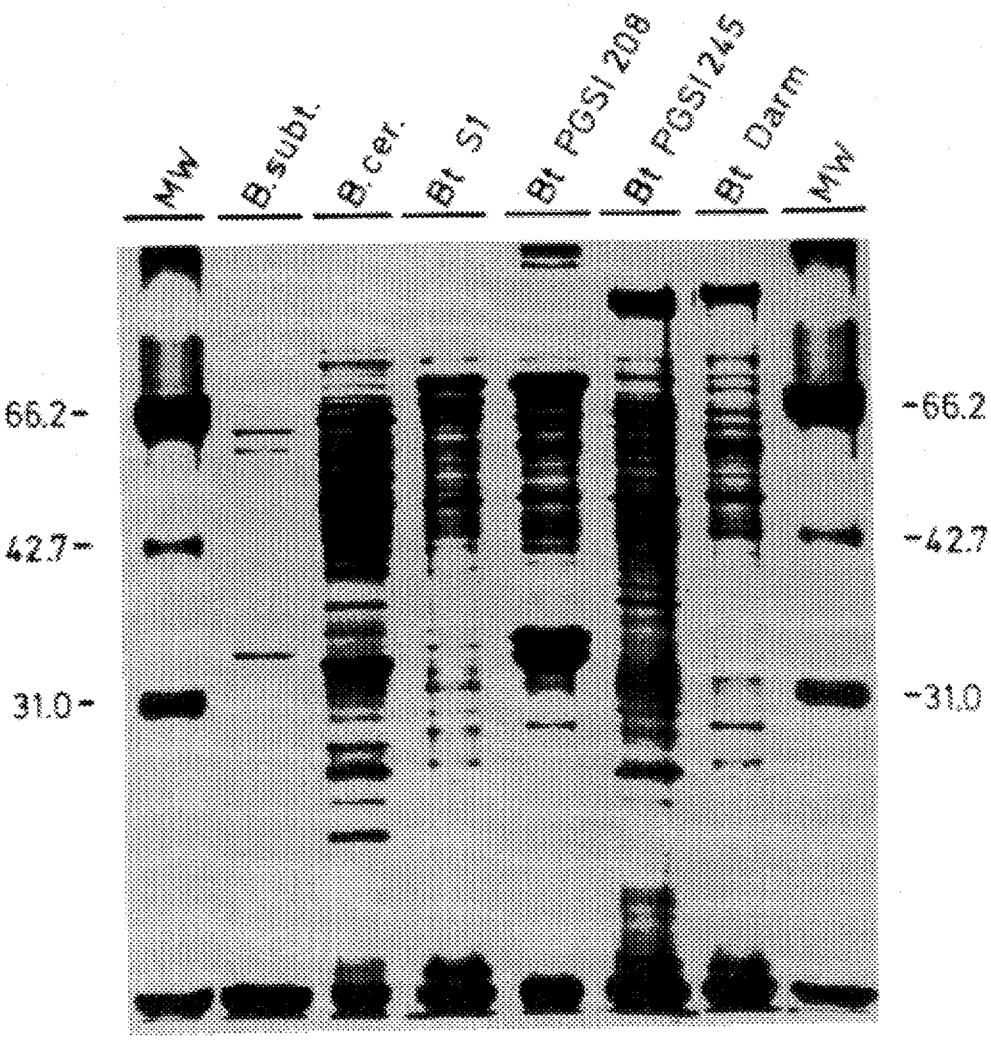
FIG. 3—Total protein patterns by SDS-PAGE of sporulated BtPGSI208 and BtPGSI245 and other Bacillus cultures. Among the comparison strains, B. subt. is *Bacillus subtilis*, B. cer. is *Bacillus cereus*, and Bt Darm is *Bacillus thuringiensis* subsp. *darmstadiensis*. These comparison strains were obtained from the sources set forth in Table 1, hereinafter. "MW" designates molecular weight markers.

Unless otherwise stated in the Examples, all procedures for making and manipulating recombinant DNA are carried out by the standardized procedures described in Maniatis et al, *Molecular Cloning—A laboratory Manual*, Cold Spring Harbor Laboratory (1982).

EXAMPLE 1

Characterization of the BtPGSI208 and BtPGSI245 strains

The BtPGSI208 strain was isolated from grain dust sampled in Belgium and was deposited at the DSM on Jan. 19, 1989 under accession No. 5131.

The BtPGSI245 strain was isolated from cow dung sampled in the United States and was deposited at the DSM on Jan. 19, 1989 under accession No. 5132.

Each strain can be cultivated on conventional standard media, preferably LB medium (Bacto-tryptone 10 g/l, yeast extract 5 g/l, NaCl 10 g/l and agar 15 g/l), preferably at 28° C. For long term storage, it is preferred to use LB liquid medium containing 50% glycerol at −70° C. or lyophilization. For sporulation, the use of $T_3$ medium (tryptone 3 g/l, tryprose 2 g/l, yeast extract 1.5 g/l, 5 mg $MnCl_2$, 0.05M $Na_2PO_4$, pH 6.8 and 1.5% agar) is preferred for 24 hours at 28° C., followed by storage at 4° C. During its vegetative phase, each of the BtPGSI208 and BtPGSI245 strains can also grow under facultative anaerobic conditions, but sporulation only occurs under aerobic conditions.

Sterilization of each strain occurs by autoclave treatment at 120° C. (1 bar pressure) for 20 minutes. Such treatment totally inactivates the spores and the crystalline BtPGSI208 and BtPGSI245 protoxins. UV radiation (254 nm) inactivates the spores but not the protoxins.

After cultivating on Nutrient Agar ("NA", Difco Laboratories, Detroit, Mich., U.S.A.) for one day, colonies of each of the BtPGSI208 and BtPGSI245 strains form opaque white colonies with irregular edges. Cells of each strain (Gram positive rods of 1.7–2.4×5.6–7.7 μm) sporulate after three days cultivation at 28° C. on NA. The crystal proteins produced during sporulation are packaged in flat rhomboid crystals in the BtPGSI208 strain and in bipyramidal crystals in the BtPGSI245 strain.

For the biochemical characterization of the two strains, the following tests were carried out using well known methods as described for example by Sheath et al (1986). Growth was observed in Nutrient Broth ("NB", Difco) supplemented with 2 and 5% NaCl. No growth of the BtPGSI208 strain and only weak growth of the BtPGSI245 strain were observed in the presence of 7% NaCl. Neither strain grew in medium supplemented with 10% NaCl. The BtPGSI208 and BtPGSI245 strains grew well on NA at 20, 28 and 37° C., but not at 4, 10 (although the BtPGSI245 strain grew slowly at this temperature), 50° and 60° C. Both strains grew in NB at pH=5, pH=6 and pH=7 and on NB containing 100 units of lysozyme (Sigma Chemical Company, St Louis, Mo., U.S.A.) per ml of NB. Growth on NA under anaerobiosis was very weak.

Metabolic characteristics of the two strains were determined using API-20E test strips (API Systems S.A., Montalieu-Vercieu, France). The results of these assays are shown in Table 1, below.

TABLE 1

Metabolic characteristics of the BtPGSI208 and BtPGSI245 strains as compared with other Bacillus strains (+ = positive reaction; − = negative reaction; w = weak reaction; nd = not determined).

| Activity | Bt PGSI 208 | Bt PGSI 245 | BTS1 | BTEN | BDAR | BCER | BSUB |
|---|---|---|---|---|---|---|---|
| ONPG | − | − | − | − | − | − | + |
| ADH | − | + | + | + | + | + | − |
| LDC | − | − | − | − | − | − | − |
| ODC | − | − | − | − | − | − | − |
| CIT | − | − | − | − | − | − | − |
| H2S | − | − | − | − | − | − | − |
| URE | − | − | − | − | − | − | − |
| TDA | − | − | − | + | w | + | + |
| IND | − | − | − | − | − | − | − |
| VP | − | − | − | w | w | w | + |
| GEL | − | + | − | + | + | + | + |
| OX | + | + | + | + | + | + | + |
| NO2 | + | + | + | + | + | + | nd |
| N2 | − | − | − | − | − | − | nd |

ONPG = p-galactosidase activity.
ADH = arginine dihydrolase activity.
LDC = lysine decar oxylase activity.
ODC = ornithine decarboxylase activity.
CIT = use of citrate as sole carbon source.
H2S = $H_2S$ formation from thiosulphate.
URE = urease activity.
TDA = tryptophan deaminase activity.
IND = indol formation from tryptophan.
VP = acetoin formation from sodium pyruvate.
GEL = gelatin liquefaction.
OX = moxidase activity.
NO2 = nitrate reduction to nitrite.
N2 = $N_2$ gas production from nitrate.
BTS1 = *Bacillus thuringiensis* BtS1 from DSM under accession no. 4288.
BTEN = *Bacillus thuringiensis* subsp. *tenebrionis* from DSM under accession no. 2803.
BDAR = *Bacillus thuringiensis* subsp. *darmstadiensis* from Institut für Landwirtschaftliche Bacteriologie und Gärungsbiologie der Eidgenössiche Technische Hochschüle, Zürich, Switzerland ("LBG"), under accession no. 4447
BCER = *Bacillus cereus* from Laboratorium voor Microbiologie, Gent, Belgium ("LMG"), under accession no. 2098.
BSUB = *Bacillus subtillis* from Agricultural Research Culture Collection, Peoria, Illinois, USA, under accession no. NRRL B-237.

Both strains were found to rapidly decompose casein in skim-milk agar and to deaminate phenylalanine in tests described by Sheath et al (1986).

Acid production from different sugars by the two strains was determined using API-50CHB test strips (API Systems SA). The results are shown in Table 2, below.

TABLE 2

Acid production by the BtPGSI208 and BtPGSI245 strains as compared with other bacilli (+ = positive reaction; − = negative reaction; w = weak reaction).

| Substrate: | Bt PGSI 208 | Bt PGSI 245 | BTS1 | BTEN | BDAR | BCER | BSUB |
|---|---|---|---|---|---|---|---|
| Control | − | − | − | − | − | − | − |
| Glycerol | − | w | + | + | + | + | + |
| Erythritol | − | − | − | − | − | − | − |
| D-arabinose | − | − | − | − | − | − | − |
| L-arabinose | − | − | − | − | − | − | + |
| Ribose | + | + | + | + | + | + | + |
| D-Xylose | − | − | − | − | − | − | + |
| L-Xylose | − | − | − | − | − | − | − |
| Adonitol | − | − | − | − | − | − | − |
| B Methyl-xyloside | − | − | − | − | − | − | − |
| Galactose | − | − | − | − | − | − | + |
| D-Glucose | + | + | + | + | + | + | + |
| D-Fructose | + | + | + | + | + | + | + |
| D-Mannose | − | + | + | + | − | − | + |
| L-Sorbose | − | − | − | − | − | − | − |
| Rhamnose | − | − | − | − | − | − | − |
| Dulcitol | − | − | − | − | − | − | − |
| Inositol | − | − | − | − | − | − | + |
| Mannitol | − | − | − | − | − | − | + |
| Sorbitol | − | − | − | − | − | − | + |
| α-Methyl-D-mannoside | − | − | − | − | − | − | − |
| α-Methyl-D-qlucoside | − | − | − | − | − | − | + |
| N-Acetyl-glucosamide | + | + | + | + | + | + | − |
| Amygdaline | − | − | − | − | − | − | + |
| Arbutine | + | + | + | + | + | − | + |
| Esculine | + | + | + | + | + | + | + |
| Salicine | + | w | − | − | − | − | + |

TABLE 2-continued

Acid production by the BtPGSI208 and BtPGSI245 strains as compared with other bacilli (+ = positive reaction; − = negative reaction; w = weak reaction).

| Substrate: | Bt PGSI 208 | Bt PGSI 245 | BTS1 | BTEN | BDAR | BCER | BSUB |
|---|---|---|---|---|---|---|---|
| Cellobiose | − | w | − | − | − | − | + |
| Maltose | + | + | + | + | + | + | + |
| Lactose | − | − | − | − | − | − | + |
| Melibiose | − | − | − | − | − | − | + |
| Saccharose | + | + | + | + | − | + | + |
| Trehalose | + | + | + | + | + | + | + |
| Inuline | − | − | − | − | − | − | + |
| Melizitose | − | − | − | − | − | − | − |
| D-Raffinose | − | − | − | − | − | − | + |
| Starch | + | + | + | + | + | + | + |
| Glycogen | + | + | + | + | + | + | + |
| Xylitol | − | − | − | − | − | − | − |
| B Gentio-biose | − | − | − | − | − | − | − |
| D-Turanose | − | − | − | − | − | − | + |
| D-Lyxose | − | − | − | − | − | − | − |
| D-Tagatose | − | − | − | − | − | − | − |
| D-Fucose | − | − | − | − | − | − | − |
| L-Fucose | − | − | − | − | − | − | − |
| D-Arabitol | − | − | − | − | − | − | − |
| L-Arabitol | − | − | − | − | − | − | − |
| Gluconate | − | − | − | − | − | − | − |
| 2 Keto-gluconate | − | − | − | − | − | − | − |
| 5 Keto-gluconate | − | − | − | − | − | − | − |

Sensitivity of the two strains towards different antibiotics was tested using Oxoid Susceptibility Test Discs on Oxoid Isosensitest agar ("CM471" of Oxoid Ltd., Basingstoke, Hampshire, England). The results are shown in Table 3, below.

TABLE 3

Antibiotic sensitivity as shown by the diameters (in mm) of inhibition zones observed after 24 hours on antibiotic-containing agar, seeded with different bacilli (R = resistant colonies or no growth detected).

| Antibiotic | amount/ disc | Bt PGSI 208 | Bt PGSI 245 | BTS1 | BTEN | BDAR | BCER | BSUB |
|---|---|---|---|---|---|---|---|---|
| Chloramphenicol | 30 ug | 25/R | 17 | 19/R | 20 | 22 | 28 | 33 |
| Bacitracin | 10 i.u | 11 | 10 | 8 | 7 | 14 | 18 | 7 |
| Gentamycin | 10 ug | 26 | 20 | 21 | 20 | 28 | 9 | 25/R |
| Neomycin | 30 ug | 24 | 20/R | 13/R | 13 | 26 | 10 | 20 |
| Tetracyclin | 30 ug | 14/R | 10 | 17/R | 16/R | 10/R | 21 | 22 |
| Carbenicillin | 100 ug | 8 | 11 | 0 | 0 | 10 | 0 | 19 |
| Rifampicin | 2 ug | 12 | 13 | 0 | 8 | 8 | 19 | 26 |
| Penicillin G | 10 i.u | 7 | 8 | 0 | 0 | 0 | 14/R | 14 |
| Streptomycin | 10 ug | 25/R | 15 | 16 | 17 | 20 | 14 | 0 |
| Spectinomycin | 10 ug | 0 | 0 | 0 | 0 | 0 | 12/R | 0 |
| Kanamycin | 30 ug | 20/R | 21/R | 0 | 0 | 24 | 15 | 24 |
| Nalidixic acid | 30 ug | 25/R | 23/R | 18/R | 25/R | 30/R | 7 | 19 |
| Sulphamethoxazole | 25 ug | 0 | 0 | 0 | 0 | 0 | 0 | 0 |
| Trimethoprin | 2.5 ug | 0 | 0 | 0 | 0 | 0 | 0 | 26 |
| Ampicillin | 10 u | 7 | 9/R | 0 | 0 | 0 | 15/R | 18 |

The enzyme spectra of the BtPGSI208 and BtPGSI245 strains were determined using the extended API-ZYM strips (API Systems S.A.). The results are shown in Table 4, below. Esterass-, peptidase- (AP1, AP2, AP3, AP4, AP5 and AP6 test strips) and osidase-test strips were inoculated with 50 ul cell suspension ($10^7$ cfu/ml). The osidase reaction was revealed after 4 hours incubation (28° C.) with 25 µl 0.1N NaOH. All other reactions were with 25 µl ZYM A and ZYM B reagent (API no. 7048).

TABLE 4

Enzymatic spectra of the BtPGSI208 and BtPGSI245 strains as compared to two other Bt strains (0 = no substrate used; 1. 2, 3, 4, 5 = 5, 10, 20, 30 and ≧40 nanomoles of substrate hydrolysed respectively).

| Substrate | Bt PGSI 208 | Bt PGSI 245 | BTS1 | BDAR |
|---|---|---|---|---|
| Esterases. | | | | |
| 2-naphtyl-valerate | 4 | 4 | 2 | 4 |
| 2-naphtyl-caproate | 5 | 5 | 5 | 5 |
| 2-naphtyl-caprylate | 5 | 5 | 5 | 5 |
| 2-naphtyl-nonanoate | 5 | 5 | 4 | 5 |
| 2-naphtyl-caprate | 5 | 3 | 3 | 5 |
| 2-naphtyl-laurate | 2 | 2 | 1 | 2 |
| 2-naphtyl-myristate | 1 | 2 | 1 | 1 |
| 2-naphtyl-palmitate | 0 | 0 | 1 | 0 |
| 2-naphtyl-stearate | 2 | 1 | 2 | 2 |
| Peptidases. | | | | |
| L-pyrrolidonyl-β-naphtylamide | 0 | 5 | 5 | 5 |
| Glycyl-β-naphtylamide | 0 | 0 | 0 | 0 |
| L-glutamyl-β-naphtylamide | 0 | 0 | 0 | 0 |
| L-leucyl-glycyl-β-naphtylamide | 0 | 1 | 0 | 0 |
| L-seryl-L-tyrosyl-β-naphtylamide | 4 | 5 | 5 | 5 |
| L-glutamine-β-naphtylamide | 1 | 5 | 4 | 5 |
| L-glutanyl-β-naphtylamide | 0 | 3 | 3 | 3 |
| Osidases. | | | | |
| Paranitrophenol-D-galactopyranoside | 0 | 0 | 0 | 0 |
| Paranitrophenol-βD-galactopyranoside | 0 | 0 | 0 | 0 |
| Paranitrophanol-aD-glucopyranoside | 5 | 5 | 5 | 5 |
| Paranitrophenol-βD-glucopyranoside | 0 | 2 | 0 | 0 |
| Paranitrophenol-a-maltoside | 2 | 4 | 3 | 5 |
| Paranitrophenol-β-maltoside | 0 | 0 | 0 | 0 |
| Paranitrophenol-N-acetyl-βD-glucosamidine | 3 | 5 | 5 | 5 |
| Paranitrophenol-βD-xylapyranoside | 0 | 0 | 0 | 0 |

EXAMPLE 2

Characteristics of the BtPGSI208 and BtPGSI245 crystals

The BtPGSI208 and BtPGSI245 strains were grown for 48 to 72 hours at 28° C. on $T_3$ medium. After sporulation, the spores and crystals were harvested in phosphate buffered saline solution ("PBS" from Oxoid Ltd.) by scraping with a Trihalski spatula. The resulting aqueous spore-crystal suspensions were centrifuged, and the pellets were resuspended and incubated overnight in aqueous solutions containing 50 mM $Na_2CO_3$ and 5 mM dithiotreitol ("DTT") at pH 10. After centrifugation, the supernatants were recovered containing the respective crystal proteins.

Figure 4A:
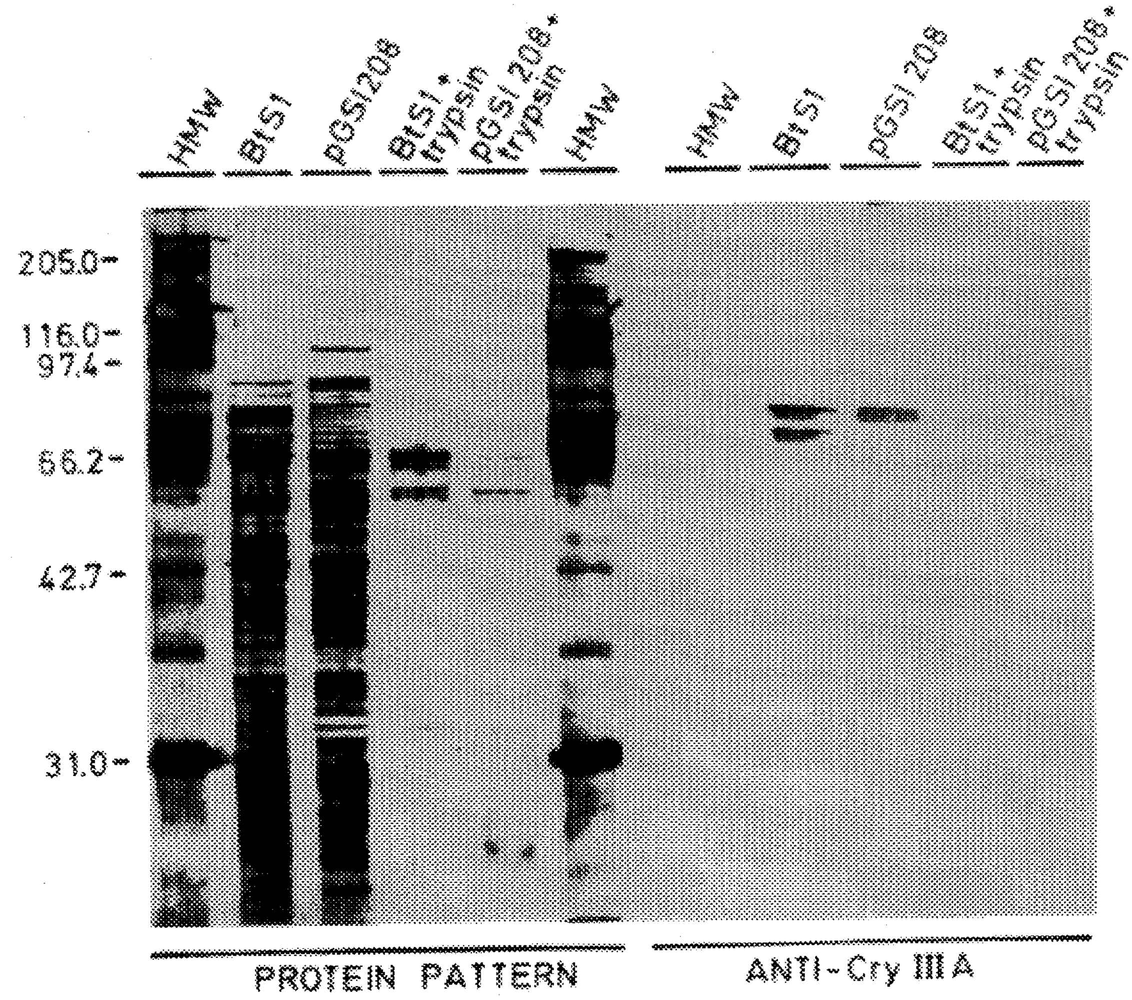
FIG. 4A—Protein blotting of total proteins and trypsinized crystal proteins from strains BtS1 and BtPGSI208. Total protein patterns were stained with Indian ink, while crystal proteins were visualized with an antiserum against Bt13 toxin ("anti-CryIIIA"). "HMW" designates molecular weight markers.
Figure 4B:
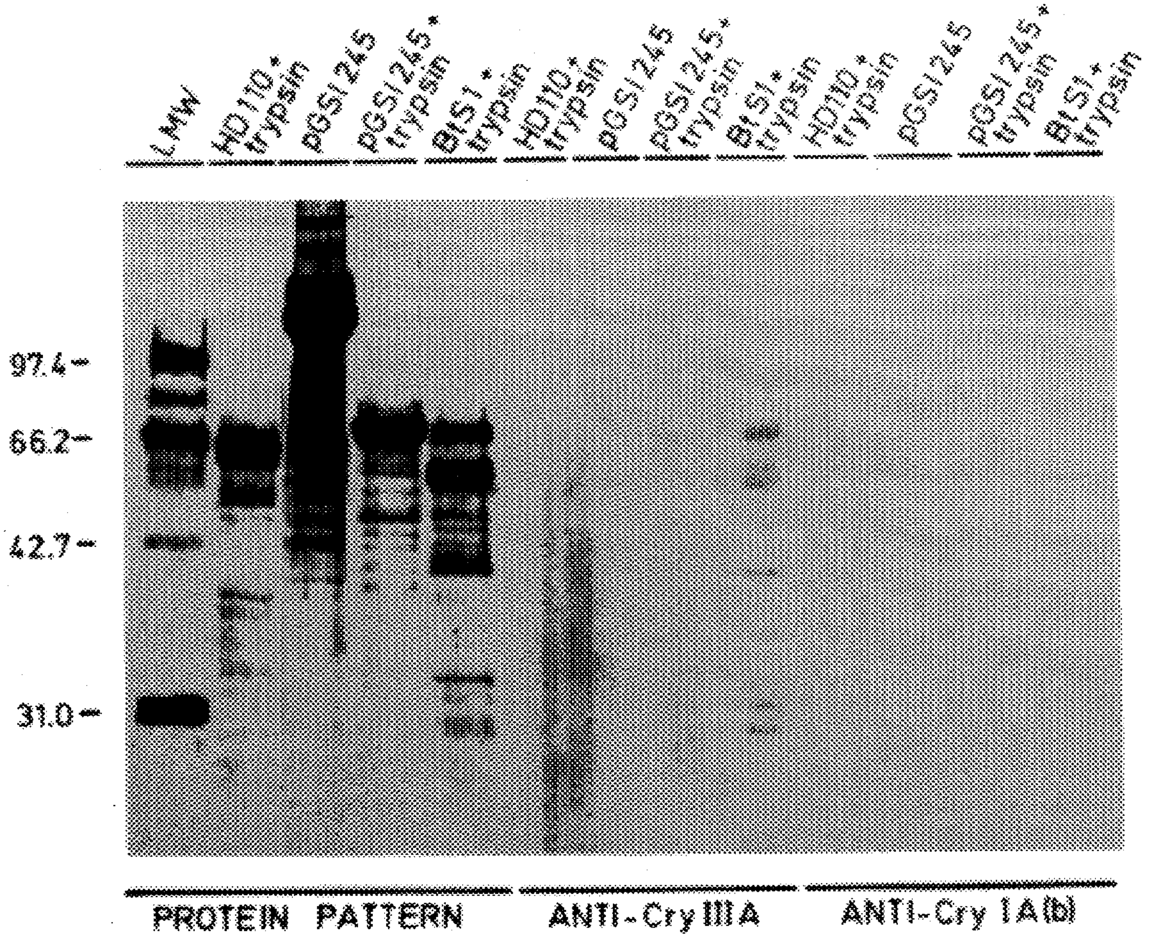
FIG. 4B—Protein blotting of total proteins and trypsinized crystal proteins from strains BtS1, BtPGSI245 and Bt HD-110. Total protein patterns were probed for their immunoreactivity with an antiserum against Bt13 toxin ("anti-CryIIIA") and an antiserum against Bt2 protoxin ("anti-CryIA(b)"). "LMW" designates molecular weight markers. The comparison strain, HD-110, was Bt HD-110, obtained from Dr. H. Dulmage, Cotton Insect Laboratories, U.S.D.A., Brownsville, Texas, U.S.A.

The BtPGSI208 protoxin and toxin, as well as the BtPGSI245 toxin, react only with a polyclonal antiserum raised against the Bt13 toxin as shown in FIGS. 4A & 4B. In contrast, the BtPGSI245 protoxin reacts with polyclonal antisera against the BtS1 or Bt13 toxin (European patent application 88/402115.5) and the Bt2 protoxin (U.S. patent application 821,582; European patent application 86/300, 291.1) as shown in FIGS. 4A and 4B.

The total protein patterns of the BtPGSI208 and BtPGSI245 strains, compared to other Bacillus strains, are shown in FIG. 3. For this comparison, the crystal proteins of each strain were analyzed on a 12.5% SDS-PAGE gel (Laemmli, 1970) and stained with Coomassie brilliant blue R-250 according to Lambert et al (1987). The crystal proteins were dissolved by exposing the spore-crystal mixtures overnight at 37° C. to 50 mM $Na_2CO_3$, pH 10, 5 mM DTT. Solubilized crystal proteins were digested by adjusting the pH to 9.0 with 0.5M HCl and by trypsinization (1 µg bovine trypsin/25 µg protein). Trypsin digestion of the BtPGSI208 and BtPGSI245 crystal proteins was performed at 37° C. overnight and revealed the presence of tryptic fragments of 68 kDa and 66 kDa, respectively (FIGS. 4A and 4B). Immunoblotting experiments, performed according to Peferoen (1988) with polyclonal antisera raised against the Bt13 toxin and the Bt2 protoxin demonstrated, in FIGS. 4A and B, that the BtPGSI208 and BtPGSI245 protoxins and toxins are immunologically related to the Bt13 toxin. In addition, the BtPGSI245 protoxin was also shown, in FIG. 4B, to be immunologically related to the Bt2 protoxin. After blotting, the proteins were stained with Indian ink (Sutherland and Skerritt, 1986) to show both immunoreactive and non-immunoreactive proteins (FIGS. 4A and 4B).

EXAMPLE 3

Insecticidal activity of the BtPGSI208 and BtPGSI245 crystal proteins

As in Example 2, both strains were grown for 48 to 72 hrs at 28° C. on $T_3$ medium. After sporulation, the spores and crystals were harvested in PBS (phosphate buffered saline) with a Trihalski spatula. The resulting spore-crystal suspensions were centrifuged, and the pellets were resuspended and incubated overnight in aqueous $Na_2CO_3$ and DTT solutions as described in Example 2. After centrifugation, the supernatants were recovered, and their contents of the respective crystal proteins of the two strains were determined.

Potato leaves were dipped in aqueous dilutions of the supernatant solutions and then air dried for two hours. Colorado potato beetle larvae of the second instar were placed on the treated leaves, and mortality of the larvae was measured after three days. These results were compared with the mortality of larvae fed leaves treated with solubilized crystal proteins of Bt HD-1 ("Bt kurstaki Dipel" from Abbott Laboratories, Abbott Park, North Chicago, Ill., U.S.A.) as a control. $LC_{50}$, expressed as ug of solubilized crystal proteins/ml, was calculated by Probit analysis (Finney, 1971). The results are summarized in Table 5, below.

TABLE 5

Comparison of toxicity of solubiliized crystal proteins from the BtPGSI208 strain, the BtPGSI245 strain and the BtHD1 strain (control) against larvae of *Leptinotarsa decemlineata*.

| Strain | LC50 | FL95min | FL95max | Slope |
|---|---|---|---|---|
| BtPGSI208 | 5.0 | 3.5 | 7.3 | 2.4 |
| BtPGSI245 | 25.1 | 14.7 | 43.3 | 1.5 |
| Control | >500 | — | — | — |

EXAMPLE 4

Identification and cloning of the btPGSI208 gene

The BtPGSI208 protoxin from the BtPGSI208 strain was detected by ELISA (Engvall and Pesce, 1978) with a polyclonal antiserum against the Bt13 coleoptera toxin (Höfte et al, 1987). The btPGSI208 gene was identified in the BtPGSI208 strain by preparing total DNA of the BtPGSI208 strain and then digesting the DNA with the restriction enzymes HindIII, EcoRI and ClaI. The so-digested DNA was analyzed by Southern blotting, probing with a nick-translated 2.9 kb HindIII fragment from the genome of the BtS1 strain (European patent application 88/402,115.5) containing the bt13 gene. After hybridization with the probe, the blot was washed under low stringency conditions (2XSSC, 0.1%SDS at 68° C. for 2×15 min), showing the presence of the btPGSI208 gene, related to the bt13 gene. The hybridization pattern with the probe also showed that the btPGSI208 gene was clearly different from the bt13 gene.

In order to isolate the btPGSI208 gene, total DNA was prepared from the BtPGSI208 strain. The total DNA preparation was partially digested with Sau3A and was size-fractionated on a sucrose gradient. Fractions containing DNA between 5 kb and 10 kb were ligated to the BglII-digested and bovine alkaline phosphatase ("BAP")-treated cloning vector pEcoR251 (Deposited at the DSM on Jul. 13, 1988 under accession number DSM 4711). Recombinant *E. coli* clones containing the vector were then screened with the 2.9 kb HindIII DNA fragment containing the bt13 gene, as a probe, to identify DNA fragments of clones containing the btPGSI208 gene. The so-identified DNA fragments were then sequenced (FIG. 1) according to Maxam and Gilbert (1980).

Based on the analysis of the DNA sequence of the btPGSI208 gene, the gene is cut with an appropriate restriction enzyme to give the truncated btPGSI208 gene, encoding the BtPGSI208 toxin of about 68 kDa.

EXAMPLE 5

Identification and cloning of the btPGSI245 gene

The BtPGSI245 protoxin from the BtPGSI245 strain was detected by ELISA (Engvall and Pesce, 1978) with a polyclonal antiserum directed against the Bt13 coleoptera toxin. Colony hybridization of the BtPGSI245 strain and Southern blotting of the BtPGSI245 total DNA, that had been probed with the 2.9 kb HindIII DNA fragment containing the bt13 gene and washed under the previously described low stringency conditions, revealed no hybridizing DNA.

Figure 2M:
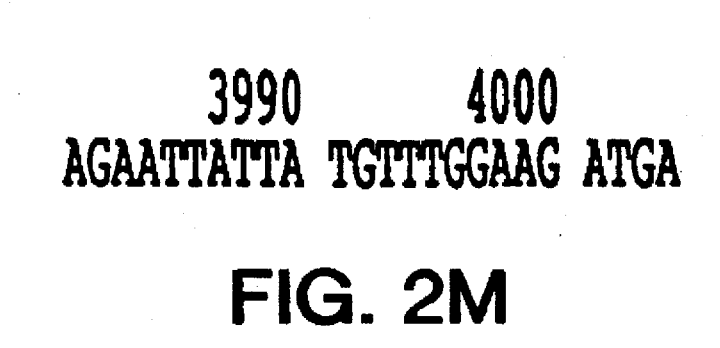

In order to isolate the btPGSI245 gene, total DNA from the BtPGSI245 strain was prepared and partially digested with Sau3A. The digested DNA was size fractionated on a sucrose gradient and fragments ranging from 5 kb to 10 kb were ligated to the BamHI-digested and BAP-treated cloning vector pUC18 (Yannisch-Perron et al, 1985). Recombinant clones containing the vector were then screened by colony immunoprobing (French et al, 1986) with an antiserum against the Bt13 toxin. Positive colonies were purified, and total protein preparations were again analyzed by immunoblotting with the antiserum against the Bt13 toxin. DNA fragments, containing the BtPGSI245 gene, from clones expressing the BtPGSI 245 protoxin, were then sequenced (FIG. 2) according to Maxam and Gilbert (1980).

Based on the analysis of the DNA sequence of the btPGSI245 gene, the gene is cut with an appropriate restriction enzyme to give the truncated btPGSI245 gene, encoding the BtPGSI245 toxin of about 66 kDa.

EXAMPLE 6

Construction of a btPGSI208-neo hybrid gene and a btPGSI245-neo hybrid gene

Following the procedure of U.S. patent application Ser. No. 821,582 and European patent applications 88/402,115.5 and 86/300291.1, the truncated btPGSI208 and btPGSI245 genes from Examples 4 and 5, respectively, are each fused to the neo gene to form the corresponding hybrid gene.

EXAMPLE 7

Insertion of the btPGSI208 and btPGSI245 genes, the truncated btPGSI208 add btPGSI245 genes and the btPGSI208-neo and btPGSI245-neo hybrid genes in *E. coli* and insertion of the truncated btPGSI208 and btPGSI245 genes and the btPGSI208-neo and btPGSI245-neo hybrid genes in potato plants The btPGSI208 and btPGSI245 genes and the truncated btPGSI208 and btPGSI245 genes from Examples 4 and 5 and the btPGSI208-neo and btPGSI245-neo hybrid genes from Example 6 are each inserted into, and expressed by, different *E. coli* in a conventional manner, using *E. coli* expression vectors as described by Botterman and Zabeau (1987). In order to express these genes in *E. coli* and in plants, different gene cassettes are made. In this regard, a BamHI restriction site is introduced at the ATG initiation codon of the btPGSI208 gene by site directed mutagenesis (Stanssens et al, 1988; Stanssens et al, 1989). The 4th nucleotide of the btPGSI208 gene is changed from an A to a G, yielding a unique BamHI site. According to the "Kozak rules" (Kozak, 1986), this mutation should also optimize the translation initiation in plant cells. In this way, the AAT codon (second codon) coding for Asn is changed into a GAT codon coding for Asp. Similarly, a NcoI is introduced at the ATG translation initiation codon of the btPGSI245 gene.

The insecticidal activity, against Colorado potato beetle second instar larvae, of the BtPGSI208 protoxin produced in *E. coli* (transformed with the btPGSI208 gene) is given in Table 6, below. Toxicity is expressed as 50% lethal concentration in ug/ml, followed by the 95% confidence interval and the slope of the probit line.

TABLE 6

| LC50 (ug/ml) | slope |
|---|---|
| 1.0 (0.6–1.8) | 2.3 |

The toxicity of the BtPGSI208 protoxin produced in *E. coli* was about 5 times greater than the toxicity of the BtPGSI208 protoxin produced by the BtPGSI208 strain. Trypsin digestion of the BtPGSI208 protoxin, produced in *E. coli*, yielded the BtPGSI208 toxin which also was active against Colorado potato beetle.

Using the procedures described in U.S. patent application Ser. No. 821,582 and European patent applications 86/300,291.1 and 88/402,115.5, the truncated btPGSI208 and btPGSI245 genes and the btPGSI208-neo and btPGSI245-neo hybrid genes are isolated and are cloned into the intermediate T-DNA vector, pGSH160 (Deblaere et al, 1988), between the vector's T-DNA terminal border repeat sequences. To provide major expression in plants, the hybrid genes and truncated genes are placed under the control of the strong constitutive promoters, Cabb-JI 35S promotor (Hull and Howell, 1987) or the TR2' promoter (Velten et al, 1984), and are fused to the transcription termination and polyadenylation signals of the octopine synthase gene (Gielen et al, 1984).

Using standard procedures (Deblaere et al, 1985), the intermediate plant expression vectors, containing the truncated btPGSI208 and btPGSI245 genes and the btPGSI208-neo and btPGSI245-neo hybrid genes, are transferred into the Agrobacterium strain C 58 C1 $Rif^R$ (US patent application Ser. No. 821,582; European patent application 86/300,291.1) carrying the disarmed Ti-plasmid pGV2260 (Vaeck et al, 1987). Selection for spectinomycin resistance yields cointegrated plasmids, consisting of pGV2260 and the respective intermediate plant expression vectors. Each of these recombinant Agrobacterium strains is then used to transform different potato plants (*Solanum tuberosum*) so that the truncated btPGSI208 gene, the truncated btPGSI245 gene, the btPGSI208-neo hybrid gene and the btPGSI245-neo hybrid gene are contained in, and expressed by, different potato plant cells.

EXAMPLE 8

Expression of the truncated btPGSI208 and btPGSI245 genes and the btPGSI208-neo and btPGSI245-neo hybrid genes in potato plants The insecticidal activity against Coleoptera of the expression products of the truncated btPGSI208 and btPGSI245 genes and the btPGSI208-neo and btPGSI245-neo hybrid genes in leaves of transformed potato plants, generated from the transformed potato plant cells of Example 7, is evaluated by recording the growth rate and mortality of *Leptinotarsa decemlineata* larvae fed on these leaves. These results are compared with the growth rate of larvae fed leaves from untransformed potato plants. Toxicity assays are performed as described in European Patent application 88/402,115.5, U.S. patent application 821,582 and European patent application 86/300,291.1. A significantly higher mortality rate is obtained among larvae fed on leaves of transformed potato plants containing the truncated btPGSI208 gene, the truncated btPGSI245 gene, the btPGSI208-neo hybrid gene or the btPGSI245-neo hybrid gene than among larvae fed the leaves of untransformed plants.

EXAMPLE 9

Transformation of a Bt strain with the endogenous btPGSI208 gene

In order to enhance its insecticidal spectrum, the BtS174A strain (Mahillon et al, 1989) is electroporated with plasmid pAMbt21R1. pAMbt21R1 is obtained by cloning the 5.4 kb HpaI fragment of plasmid pJL21 into the EcoRV site of the tetracycline resistance gene of the shuttle vector pAM401 (Wirth et al, 1987). Plasmid pJL21 is obtained by cloning a 6 kb fragment, containing the btPGSI208 gene, from the BtPGSI208 strain into the BglIII site of plasmid pEcoR251 (DSM accession no. 4711).

The electroporation procedure is carried out as described in PCT patent application no. PCT/EP89/01539. The BtS174A strain, transformed with pAMbt21R1, retains its insecticidal activity against Lepidoptera and demonstrates a newly acquired insecticidal activity against Coleoptera due to expression of the btPGSI208 gene in the strain.

Needless to say, this invention is not limited to the BtPGSI208 (DSM 5131) strain and the BtPGSI245 (DSM 5132) strain. Rather, the invention also includes any mutant or variant of the BtPGSI208 or BtPGSI245 strain which produces crystals, crystal proteins, protoxin or toxin having substantially the same properties as the BtPGSI208 or BtPGSI245 crystals, crystal proteins, protoxin or toxin. In this regard, variants of the BtPGSI208 and BtPGSI245 strains include variants whose total protein pattern is substantially the same as the protein pattern of either the BtPGSI208 strain or the BtPGSI245 strain as shown in FIG. 3.

This invention also is not limited to potato plants transformed with the truncated btPGSI208 or btPGSI245 gene. It includes any plant, such as tomato, tobacco, rapeseed, alfalfa, sunflowers, cotton, corn, soybeans, brassicas, sugar beets and other vegetables, transformed with an insecticidally effective part of the btPGSI208 or btPGSI245 gene.

Nor is this invention limited to the use of *Agrobacterium tumefaciens* Ti-plasmids for transforming plant cells with an insecticidally effective btPGSI208 or btPGSI245 gene part. Other known techniques for plant cell transformations, such as by means of liposomes, by electroporation or by vector systems based on plant viruses or pollen, can be used for transforming monocotyledons and dicotyledons with such a gene part.

Furthermore, DNA sequences other than those shown in FIG. 1 for the btPGSI208 gene and the truncated btPGSI208 gene and in FIG. 2 for the btPGSI245 gene and the truncated btPGSI245 gene can be used for transforming plants and bacteria. In this regard, the DNA sequence of FIG. 1 or 2 can be modified by: 1) replacing some codons with others that code either for the same amino acids or for other amino acids; and/or 2) deleting or adding some codons; provided that such modifications do not substantially alter the properties of the encoded, insecticidally effective portion of the BtPGSI208 or BtPGSI245 protoxin or toxin.

Also, other DNA recombinants containing the aforementioned DNA sequences in association with other foreign DNA, particularly the DNA of vectors suitable for transforming plants and microorganisms other than *E. coli*, are encompassed by this invention. In this regard, this invention is not limited to the specific plasmids containing the btPGSI208 and btPGSI245 genes, or parts thereof, that were heretofore described, but rather, this invention encompasses any DNA recombinants containing a DNA sequence that is their equivalent. Further, the invention relates to all DNA recombinants that include all or part of either the btPGSI208 gene or the btPGSI245 gene and that are suitable for transforming microorganisms (e.g., plant associated bacteria such as *Bacillus subtilis*, Pseudomonas and Xanthomonas or yeasts such as *Streptomyces cerevisiae*) under conditions which enable all or part of the gene to be expressed and to be recoverable from said microorganisms or to be transferred to a plant cell.

REFERENCES

Botterman and Zabeau, DNA 6, 583–591 (1987)

Deblaere, R., Bijtebier, B. De Greve, H., Debock, F., Schell, J., Van Montagu, M. and Leemans, J., Nucleic Acids Research 13, 4777–4788 (1985)

Deblaere, R., Reynaerts A., Höfte H., Hernalsteens J. -P., Leemans J. and Van Montagu M., Methods in Enzymology 153, 277–292 (1988).

Dulmage, H. T., "Production of Bacteria for Biological Control of Insects" in *Biological Control in Crop Production*, Ed. Paparizas, D. C., Osmun Publishers, Totowa, N.J., U.S.A., pp. 129–141 (1981).

Ellar, D. J., Knowles, B. H., Drobniewski, S. A. and Haider, M. Z., in "Fundamental and Applied aspects of Invertebrate Pathology". Ed. Samson, R. A., Vlak, J. M. and Peters, D. (1986) pp. 7–10. Wageningen, Foundation of the fourth International Colloqium of Invertebrate Pathology.

Engvall and Pesce, Scand. Immunol. Suppl. 7 (1978)

Finney, Probit Analysis, 3rd Edition, Cambridge University Press (1971)

Franck, Guilley, Jonard, Richards and Hirth, Cell 21, 285–294 (1980)

French, B. T., Maul, H. N. and Maul, G. G., Anal.Biochem. 156, 417423 (1986)

Gardner, Howarth, Hahn, Brown-Luedi, Shepard and Messing, Nucleic Acids Research 9, 2871–2887 (1981)

Gielen, J., De Beukeleer, M., Seurinck, J., Deboeck, F., De Greve, H., Lemmers, M., Van Montagu, M. and Schell, J., EMBO J 3, 835–845 (1984).

Goldberg, R. B., Science 240, 1460–1467 (1988)

Höfte, H., De Greve, H., Seurinck, J., Jansens, S., Mahillon, J., Ampe, Vandekerckhove, J, Vanderbruggen, H., Van Montagu, M., Zabeau, M. and Vaeck, M., Eur. J. Biochem. 161, 273–280 (1986)

Höfte, H., Seurinck, J., Van Houtven A. and Vaeck, M., Nucleic Acids Research 15, 7183 (1987)

Höfte, H., Dissertation thesis at the State University of Ghent, Belgium (1988).

Höfte, H., Van Rie, J., Jansens, S., Van Houtven, A., Verbruggen, H. and Vaeck, M., Applied and Environmental Microbiology 54, 2010–2017 (1988)

Höfte H. and Whiteley H. R., Microbiological Review 53, 242–255 (1989).

Hull and Howell, Virology 86, 482–493 (1987)

Kozak M., Cell 44, 283–292 (1986).

Kuhlemeier, Green and Chua, Ann. Rev. Plant Physiol. 38, 221–257 (1987)

Laemmli V., Nature 227, 680–685 (1970)

Lambert, B., Leyns, F., Van Rooyen, L., Gossele, F., Papon, Y. and Swings, J. Applied and Environmental Microbiology 53, 1866–1871 (1987)

Mahillon, J. and Delcour, J., J. Microbiol. Methods 3, 69–73 (1984)

Mahillon et al, FEES Microbiology Letters 60, 205–210 (1989)

Maxam, A. M. and Gilbert, W., Methods in Enzymol. 65, 499–560 (1980).

Odell, J. T., Nagy, J., and Chua, N., Nature 313, 810–812 (1988).

Peferoen, M. in Methods in Molecular Biology, vol. 3: New Protein Techniques, p. 395–402, Ed. John M. Walker, Humana Press (1988).

Reiss, B., Sprengel, R., Will, H. and Schaller, H., Gene 30, 217–223 (1984)

Sneath, P., Mair, N., Sharpe, M. and Holt, J., (1986) in Bergey's Manual of Systematic Bacteriology, Vol. 2, pp. 1104–1139. Eds. Williams and Wilkins, Baltimore, London.

Stanssens P., McKeown Y., Friedrich K. and Fritz H. J. (1988), "Oligonucleotide-directed construction of mutations by the gapped duplex DNA method using the pMA/c plasmid vectors", published in the collection of additional experimental procedures distributed at the EMBO laboratory course on "Directed mutagenesis and protein engineering" in July 1987 at the Max Planck Institute für Biochemie, Martinsried, Federal Republic of Germany.

Stanssens P., Opsomer C., McKeown Y., Kramer W., Zabeau M. and Fritz H. J., Nucleic Acids Research 12, 4441–4454 (1989).

Sutherland, M. W. and Skerritt, J. M., Electrophoresis, 7, 401–406 (1986)

Vaeck, M., Reynaerts, A., Höfte, H., Jansens, S., De Beuckeleer, M., Dean, C., Zabeau, M., Van Montagu, M. and Leemans, J., Nature 327, 33–37(1987).

Velten, J., Velten, L., Hain, R. and Schell, J., EMBO J 3, 2723–2730 (1984).

Velten, J. and Schell, J. Nucleic Acids Research 13, 6981–6998 (1985)

Wirth, R., An, F. and Clewell, D. B. in "Streptococcus Genetics" (Ferreti J. J. and Curtiss III, R., eds.), pp. 25–27, American Society for Microbiology, Washington D.C. (1987).

Yanntsch-Perron, C., Vierra, J. and Messing, J., Gene 33, 103–119 (1985).

We claim:

1. An isolated BtPGSI245 strain which was deposited under DSM accession no. 5132 or a strain having all of the identifying phenotypical characteristics of said BtPGSI245 strain, having activity against insects of the family Coleoptera.

2. Isolated BtPGSI245 crystals or crystal proteins comprising a toxin or protoxin having activity against insects of the family Coleoptera produced by the BtPGSI245 strain of claim 1.

3. Isolated BtPGSI245 protoxin comprising about amino acids 1–1138 of FIG. 2.

4. An insecticidal composition having activity against Coleoptera, which comprises the isolated BtPGSI245 strain of claim 1.

5. A process for controlling a Coleopteran pest comprising contacting said pest with an insecticidally effective amount of the insecticidal composition of claim 4.

6. The process of claim 5 wherein said Coleopteran pest is *Leptinotarsa decemlineata, Agelastica alni, Diabrotica luteola, Haltica tombacina, Anthonomus grandis, Tenebrio molitor, Diabrotica undecimpunctata* or *Triboleum castaneum.*

7. The process of claim 6 wherein the pest is *Leptinotarsa decemlineata.*

8. An insecticidal composition having activity against Coleoptera which comprises the isolated BtPGSI245 crystals or crystal proteins of claim 2.

9. An insecticidal composition having activity against Coleoptera which comprises the isolated BtPGSI245 protoxin of claim 3.

10. Isolated BtPGSI245 toxin comprising about amino acids 53–637 of FIG. 2.

11. An insecticidal composition having activity against Coleoptera which comprises the isolated BtPGSI245 toxin of claim 10.

12. A process for controlling a Coleopteran pest comprising contacting said pest with an insecticidally effective amount of the insecticidal composition of claim 8.

13. A process for controlling a Coleopteran pest comprising contacting said pest with an insecticidally effective amount of the insecticidal composition of claim 9.

14. A process for controlling a Coleopteran pest comprising contacting said pest with an insecticidally effective amount of the insecticidal composition of claim 11.

* * * * *